(12) United States Patent
Horne et al.

(10) Patent No.: US 7,615,638 B2
(45) Date of Patent: Nov. 10, 2009

(54) SYNTHESIS OF GROSSULARINES-1 AND ANALOGS THEREOF AND METHOD OF USE

(75) Inventors: David A. Horne, Altadena, CA (US);
Richard Jove, Glendora, CA (US);
Sangkil Nam, Monrovia, CA (US);
Kenichi Yakushijin, Monrovia, CA (US); Fumiko Y. Yakushijin, Monrovia, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 11/742,383

(22) Filed: Apr. 30, 2007

(65) Prior Publication Data

US 2008/0033004 A1    Feb. 7, 2008

Related U.S. Application Data

(60) Provisional application No. 60/795,679, filed on Apr. 28, 2006.

(51) Int. Cl.
*C07D 471/22* (2006.01)
*C07D 487/22* (2006.01)

(52) U.S. Cl. ................................... 546/64
(58) Field of Classification Search ............ 546/64
See application file for complete search history.

(56) References Cited

OTHER PUBLICATIONS

Miyake, Fumiko Y. Biomimetic Synthesis of Grossularines-1, Angew. Chem. Int. Ed. 44 (2005) 3280-3282.*
Abas, S. A., et al., "Alkaloids from the Tunicate *Polycarpa aurata* from Chuuk Atoll," J. Org. Chem., 61:2709-2712 (1996).
Barrios-Sosa, A. C., et al., "A Practical Synthesis of (Z)-Debromohymenialdisine," J. Org. Chem. 65:610-611 (2000).
Barrios-Sosa, A. C., et al., "Synthesis of Axinohydantoins," J. Org. Chem. 67:4498-4500 (2002).
Choshi, T., et al., "Total Synthesis of Grossularines-1 and -2," J. Org. Chem., 60:5899-5904 (1995).
Dalkafouki, A., et al., "Synthesis of 2-Dimethylaminoimidazole Derivatives: A New Access to Indolyl-imidazole Alkaloids of Marine Origin," Tetrahedron Lett. 32:5325-5328 (1991).
Guyot, M., et al., "An 3-Indolyl-imidazol-4-one from the Tunicate *Dendrodoa grossularia*," Tetrahedron Lett. 27:2621-2622 (1986).
Helbecque, N., et al., "Grossularine-1 and Grossularine-2, alphaCarbolines from *Dendrodoa grossularia*, as Possible Intercalative Agents," Cancer Biochem. Biophys., 9:271-279 (1987).
Lahue, B.R., et al., "Dienophilicity of Imidazole in Inverse Electron Demand Diels—Alder Reactions. 4. Intermolecular Reactions with 1,2,4-Triazines," J. Org. Chem., 68:4345-4354 (2003).
Lancini, G. C., et al., "A New Synthesis of Alkyl and Aryl 2-Aminoimidazoles," J. Heterocycl. Chem. 3:152-154 (1966).
Lawson, A., "The Reaction of Cyanamide with alpha-Amino-acetals and alpha-Amino-aldehydes," J. Chem. Soc. 307-310 (1956).
Loukaci, A., et al., "Revised Assignments of the 13C NMR Spectra of Crossularine-1 and -2 Using 2D Heteronuclear 1H—13C Correlations," Mag. Res. Chem. 34:143-145 (1996).
Miyake, F. Y., et al., "A Concise Synthesis of Topsentin A and Nortopsentins B and D," Org. Lett. 2:2121-2123 (2000).
Miyake, F. Y., et al., "A Facile Synthesis of Dragmacidin B and 2,5-Bis(6'-bromo-3'-indolyl)piperazine," Org. Lett. 2:3185-3187 (2000).
Miyake, F. Y., et al., "Synthesis of Marine Sponge Bisindole Alkaloids Dihydrohamcanthins," Org. Lett. 4:941-943 (2002).
Molina, P., et al., "Investigative Studies on the Formation of the Imidazo [4',5':3,4]pyrido[2,3-b]indole Ring: Formal Synthesis of the Alkaloids Grossularines-1 and 2. X-Ray Crystal Structures of 5-Indol-3-yl-imidzole and Bisimidazo-carbazole Derivatives," Tetrahedron 54:9623-9638 (1998).
Moquin-Pattey, C., et al., "Grossularine-1 and Grossularine-2, Cytotoxic alpha-Carbolines from the Tunicate: *Dendrodoa grossularia*," Tetrahedron, 45:3445-3450 (1989).
Olofson, A., et al., "Synthesis of Marine Sponge Alkaloids Oroidin, Clathrodin, and Dispacamides. Preparation and Transformation of 2-Amino-4,5-dialkoxy-4,5-dihydroimidazolines from 2-Aminoimidazoles," J. Org. Chem. 63:1248-1253 (1998).
Singh, S., et al., "Autoxidation of the Indolic Neurotixin 5,6-Dihydroxytryptamine," J. Org. Chem., 55:1484-1489 (1990).

* cited by examiner

*Primary Examiner*—Kamal A Saeed
*Assistant Examiner*—Samantha L Shterengarts
(74) *Attorney, Agent, or Firm*—Joseph P. Hamilton; Perkins Coie LLP

(57) ABSTRACT

In one embodiment of the present invention, a synthesis of grossularine-1 and N,N-didesmethylgrossularine-1 2 and analogs thereof based on a novel oxidative dimerization-electrocyclization sequence of 2-amino-4-(3-indolyl)imidazoles derived from oxotryptamine 3 is described.

16 Claims, 37 Drawing Sheets grossularine-1 (1) R=Me
*N,N*-didesmethylgrossularine-1 (2) R=H

3

4

(eq. 1)

Compound grossularine-1 1

$IC_{50} = 10.3$ μM

Compound N,N-didesmethylgrossularine-1 2

$IC_{50}$ = 7.3 μM

Compound α-carboline 8

IC$_{50}$ = 1.8 μM

Compound imine 10

IC$_{50}$ = 7.6 µM

5

$^1$H NMR, $d_6$-DMSO

N,N-diethyl-pre-grossularine-1 11, where R=NEt$_2$ piperidinyl-pre-grossularine-1 13, where R=

N,N-diethyl-grossularine-1 12, where R=NEt$_2$ piperidinyl-grossularine-1 14, where R=

Compound N,N-diethyl-pre-grossularine-1 11

Compound N,N-diethyl-grossularine-1 12

Compound piperidinyl-pre-grossularine-1 13

Compound piperidinyl-grossularine-1 14

Compound grossularine-1 1

SYNTHESIS OF GROSSULARINES-1 AND ANALOGS THEREOF AND METHOD OF USE

CROSS-REFERENCE TO RELATED APPLICATIONS

This application claims the benefit of U.S. Provisional Patent Application Ser. No. 60/795,679, filed Apr. 28, 2006, which is incorporated herein by reference.

GOVERNMENT SUPPORT

This invention was made with government support under NIH Grant No. GM 71985 awarded by the National Institutes of Health. The government has certain rights in the invention.

FIELD OF THE INVENTION

The present invention relates to methods of synthesis and methods of use of grossularines-1 and analogs thereof.

BACKGROUND OF THE INVENTION

Referring to FIG. 1, isolated in only small amounts from the Britannia marine tunicate *Dendrodoa grossularia* (Styelidae), grossularine-1 1 represents one of the more structurally intriguing members of a relatively small but potent class of α-carboline metabolites that exhibit pronounced effects against solid human tumor cell lines.[1] Closely related to grossularine-1 1 is N,N-didesmethylgrossularine-1 2 (from the Chuuk Atoll tunicate *Polycarpa aurata*) whose structure was established by X-ray crystallographic analysis.[2]

In contrast to the well-known class of β-carboline-derived natural products, grossularines represent the first examples of naturally occurring α-carbolines. Despite the promising biological activity of grossularine-1 1, only one total synthesis has been completed.[3] In Hibino's approach, the construction of the tetracyclic pyrido[2,3-b]indole ring system proceeded in a linear manner through the use of Pd-catalyzed cross-coupling reactions of halogenated indoles and metallated imidazoles. A formal synthesis of grossularine-1 1 has been reported by Molina that intersects Hibino's key intermediate.[4] The limited material available from nature as well as synthetic sources, however, have hampered further investigations in vivo.

Accordingly, improved methods for the synthesis of grossularine-1 1 and N,N-didesmethylgrossularine-1 2 and methods for use of said compounds are desired.

SUMMARY OF THE INVENTION

In one embodiment of the invention, a synthesis of grossularine-1 and N,N-didesmethylgrossularine-1 2 is described based on a oxidative dimerization-electrocyclization sequence of 2-amino-4-(3-indolyl)imidazoles derived from oxotryptamine 3.

In another embodiment of the invention a method of synthesizing grossularine-1 1 is described comprising: condensing oxotryptamine 3 and dimethylcynamide in the absence of air to produce 2-dimethylamino-4-(3-indolyl)imidazole 5 as an HCl salt; exposing 2-dimethylamino-4-(3-indolyl)imidazole 5.HCL to an ammonia saturated methanol solution in air to produce α-carboline imine 8; and exposing α-carboline 8 to hydrolosis conditions to produce grossularine-1 1.

In another embodiment of the invention, a method of synthesizing N,N-didesmethylgrossularine-1 2 is described comprising: condensing oxotryptamine 3 and cyanamide in the absence of air to produce 2-amino-4-(3-indolyl)imidazole 6; exposing 2-amino-4-(3-indolyl)imidazole 6 to an ammonia saturated methanol solution in air to produce imine 10; and exposing imine 10 to hydrolosis conditions to produce N,N-didesmethylgrossularine-1 2.

DETAILED DESCRIPTION

In order to fully understand the manner in which the above-recited details and other advantages and objects according to the invention are obtained, a more detailed description of the invention will be rendered by reference to specific embodiments thereof.

In one embodiment, a synthesis of grossularine-1 1 and N,N-didesmethylgrossularine-1 2 based on a novel oxidative dimerization-electrocyclization sequence of 2-amino-4-(3-indolyl)imidazoles 5 and 6 derived from oxotryptamine 3 is described.

Figure 1:
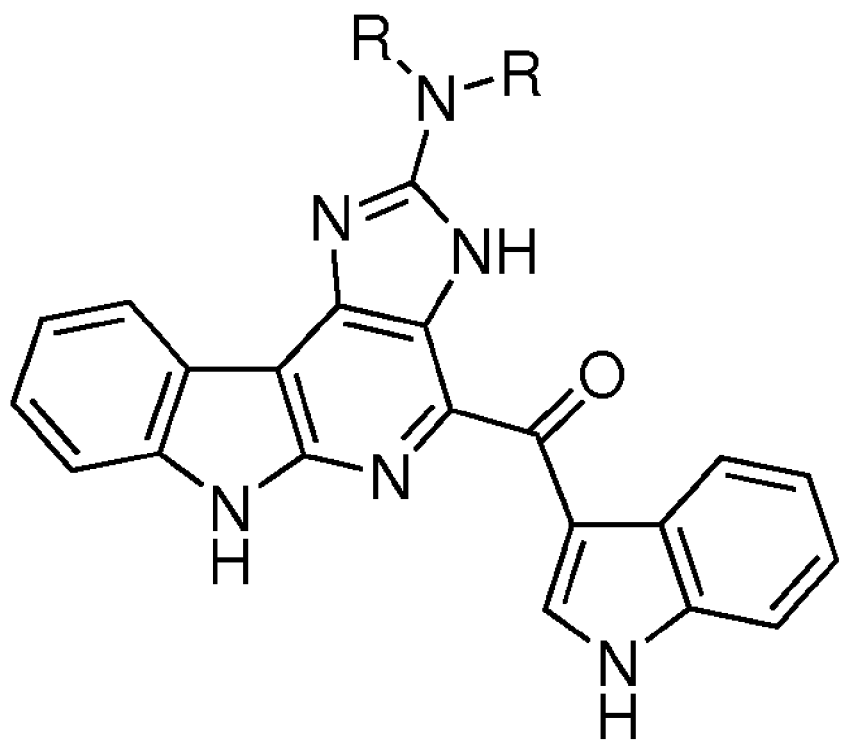
FIG. 1 shows grossularine-1 1 and N,N-didesmethylgrossularine-1 2.
Figure 2:
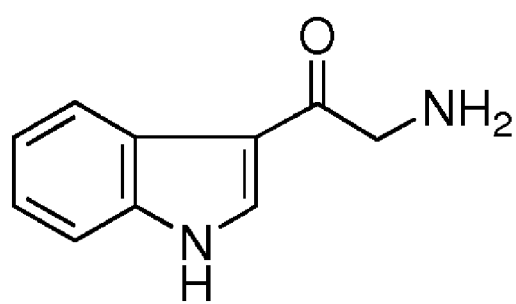
FIG. 2 shows oxotryptamine 3 and 2-dimethylamino-5-(3-indolyl)imidazol-4-one 4.21
Figure 2:
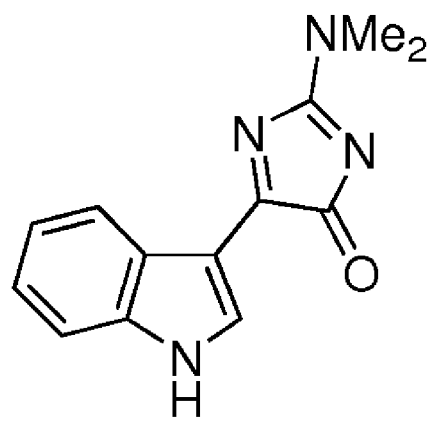
Figure 3:
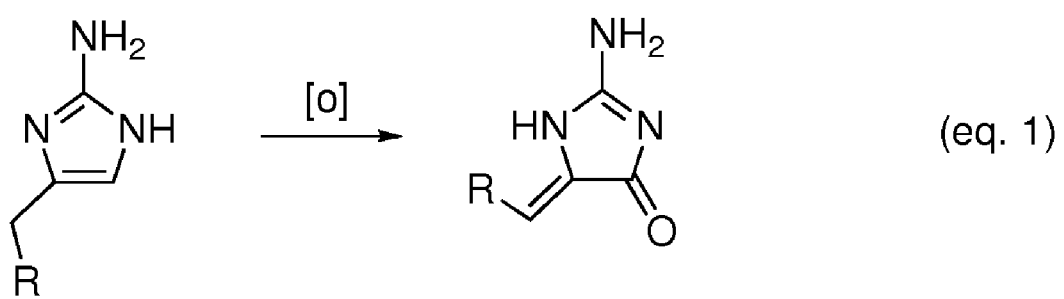
FIG. 3 shows that 2-aminoimidazoles may be converted to imidazolones via oxidation.

Referring to FIG. 2, oxotryptamine 3 continues to serve as an important cornerstone in indole heterocyclic construction. A practical procedure for the preparation of oxotryptamine 3 that avoids the use of protecting groups and DDQ oxidation and that may be applied to the synthesis of various bis-indole marine natural products is known.[5] In a formal sense, grossularine 1 and its didesmethyl congener 2 are comprised of two oxotryptamine units that are linked via an oxidative coupling between the two carbon centers of the amino bearing termini. Although such a mode of dimerization is difficult to envisage with oxotryptamine per se, the use of an electron-rich aromatic surrogate based on 2-aminoimidazoles 5 and 6 is possible, particularly in view of the oxidized analog, 2-dimethylamino-5-(3-indolyl)imidazol-4-one 4,[6] which was coisolated with grossularine-1 1 from the same tunicate. Further, referring to FIG. 3, 2-aminoimidazoles may be converted to imidazolones via oxidation (eq. 1).[7]

Figure 4:
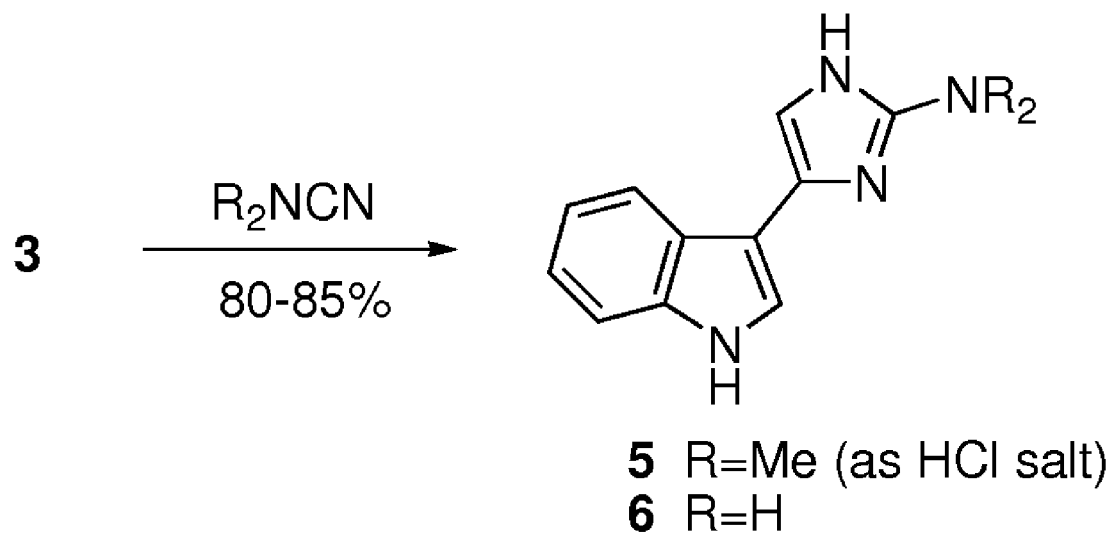
FIG. 4 shows preparation of 2-aminoimidazoles 5 and 6 (scheme 1) by utilizing the cyclocondensation of α-amino carbonyl compounds and cyanamide.

Referring to FIG. 4 the synthesis of the present embodiment begins with the preparation of 2-aminoimidazoles 5 and 6 by utilizing the cyclocondensation of α-amino carbonyl compounds and cyanamide.[8] Condensation of oxotryptamine 3 and dimethylcyanamide in the absence of air produces 2-dimethylamino-4-(3-indolyl)imidazole 5. Note that the structural identity for all new compounds was established on the basis of $^1$H and $^{13}$C NMR and high resolution mass spectral analysis. Further, note that in contrast to the more commonly observed 2-aminoimidazole unit found in nature, the N,N-dimethylaminoimidazole derivative has been less frequently encountered. A five step synthesis of N,N-dimethylaminoimidazole from benzyl isocyanate has been described.[9] While it is difficult to purify 2-dimethylamino-4-(3-indolyl)imidazole 5 as the free base by flash chromatography due to its instability, 2-dimethylamino-4-(3-indolyl)imidazole 5 can be obtained in relatively pure form as the hydrochloride salt. 2-amino-4-(3-indolyl)imidazole 6, which lacks the dimethyl substituent, can be secured as the free base via condensation of oxotryptamine 3 with cyanamide followed by chromatographic purification over silica.

Figure 5:
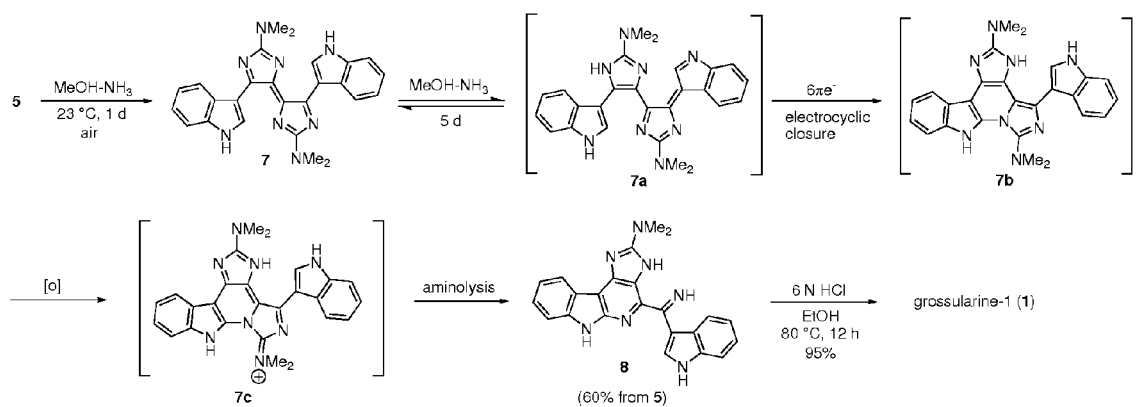
FIG. 5 shows that upon exposure of 2-dimethylamino-4-(3-indolyl)imidazole 5.HCl to a methanol solution saturated with ammonia, α-carboline imine 8 is produced.

The instability of 2-dimethylamino-4-(3-indolyl)imidazole 5 normally would not be judged very significant on its own. Referring to FIG. 5, unexpectedly, upon exposure of 2-dimethylamino-4-(3-indolyl)imidazole 5.HCl to a methanol solution saturated with ammonia, α-carboline 8 was produced. Autooxidation of 2-dimethylamino-4-(3-indolyl)imidazole 5.HCl took place upon standing in a MeOH solution in air to yield 2-dimethylamino-5-(3-indolyl)imidazol-4-one 4 as a yellow solid which was identical, by spectral comparison of $^1$H and $^{13}$C NMR data, to natural and synthetic material reported in references 6 and 9, respectively. During the course of the reaction, dimer 7 partially precipitated from solution after 1 day as a dark violet solid. Collection and resubjection of dimer 7 to the reaction conditions afforded α-carboline 8. One mechanistic pathway that might account for the above involves the initial oxidative dimerization of 2-dimethylamino-4-(3-indolyl)imidazole 5 to yield dimer 7. Upon standing in a methanol-saturated ammonia solution in air, dimer 7 undergoes an electrocyclization-aromatization event via tautomer 7a. Oxidation of the resulting intermediate 7b to 7c followed by facile aminolysis results in loss of dimethylguanidine and the formation of α-carboline 8. The sequence is remarkably efficient, delivering 8 directly in one pot and good overall yield from 2-dimethylamino-4-(3-indolyl)imidazole 5. Aromatic α-carboline imine 8 was found to be quite stable and required fairly rigorous hydrolysis conditions to yield grossularine-1 1 as a yellow solid. All spectral data of synthetic grossularine-1 1 were in excellent agreement with data reported for the natural product.[1]

Figure 6:
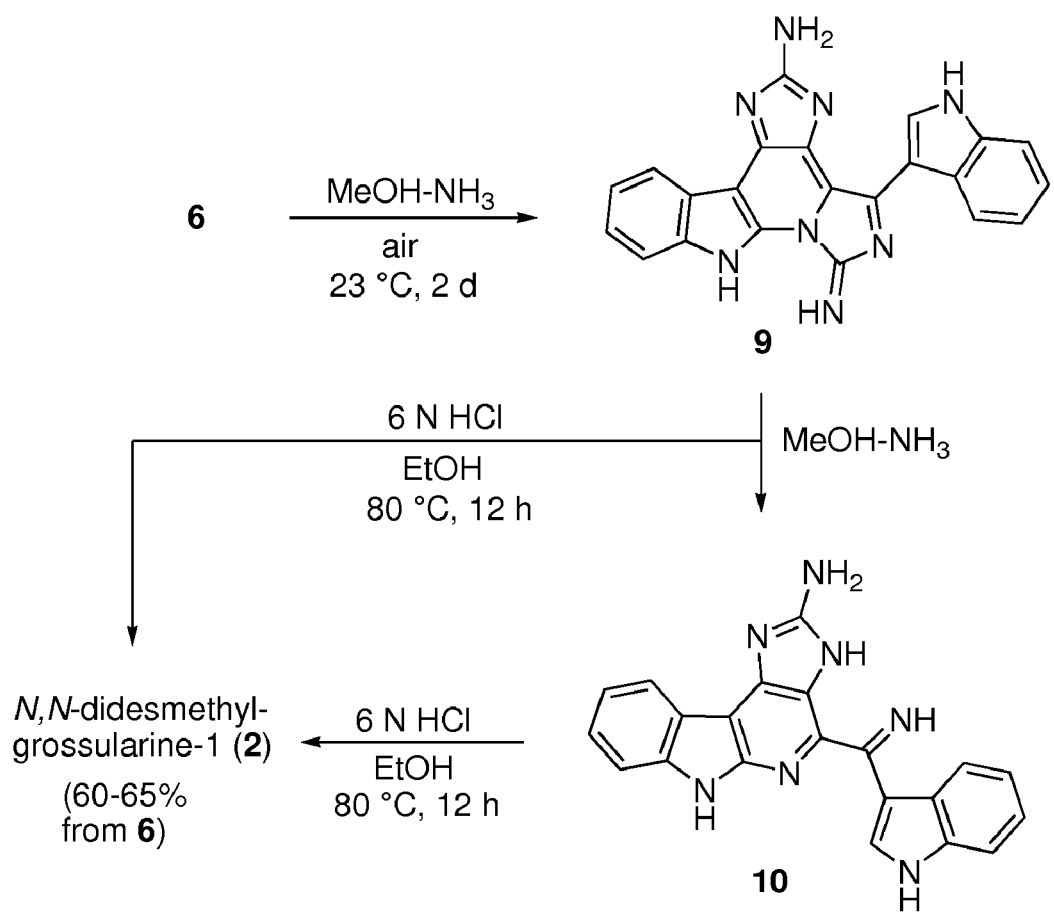
FIG. 6 shows that treatment of 2-amino-4-(3-indolyl)imidazole 6 under MeOH—$NH_3$ conditions produces fused pentacyclic dimer 9.

Referring to FIG. 6, similarly, treatment of 2-amino-4-(3-indolyl)imidazole 6 under analogous MeOH—NH$_3$ conditions in air produced fused pentacyclic dimer 9 as a dark-violet to black solid. Upon further standing in MeOH—NH$_3$, dimer 9 underwent aminolysis to afford imine 10. Hydrolysis of the imine functionality of imine 10 gave N,N-didesmethylgrossularine-1 2. Alternatively, N,N-didesmethylgrossularine-1 2 can be obtained directly from the hydrolysis of dimer 9. All spectral data of synthetic N,N-didesmethylgrossularine-1 2 were in excellent agreement with those reported for the natural product.[2] In noting differences between dimethylaminoimidazole 5 and its desmethyl amino analog 6, the precyclized desmethylamino dimer corresponding to dimer 7 was not obtained in the case of 2-amino-4-(3-indolyl)imidazole 6. This outcome is attributed to the greater solubility of the putative desmethyl intermediate in methanolic ammonia. In the case of 2-dimethylamino-4-(3-indolyl)imidazole 5, N,N-dimethylamino analog 7c corresponding to dimer 9 also was not obtained. The greater propensity towards aminolysis of this putative guanidinium ion intermediate accounts for this result.

Although electron-rich aromatic heterocycles such as indoles are known to undergo autooxidative coupling,[11] the oxidative dimerization of 2-aminoimidazoles under simple aerobic conditions is unprecedented. The structurally and biologically significant α-carboline natural products grossularine-1 1 and N,N-didesmethylgrossularine-1 2 were produced in excellent overall yields using an operationally simple, three-pot sequence starting from oxotryptamine. The chemistry and brevity of this novel sequence support a plausible biogenetic connection that accounts for these and several other structurally related members this α-carboline family.

Figure 7:
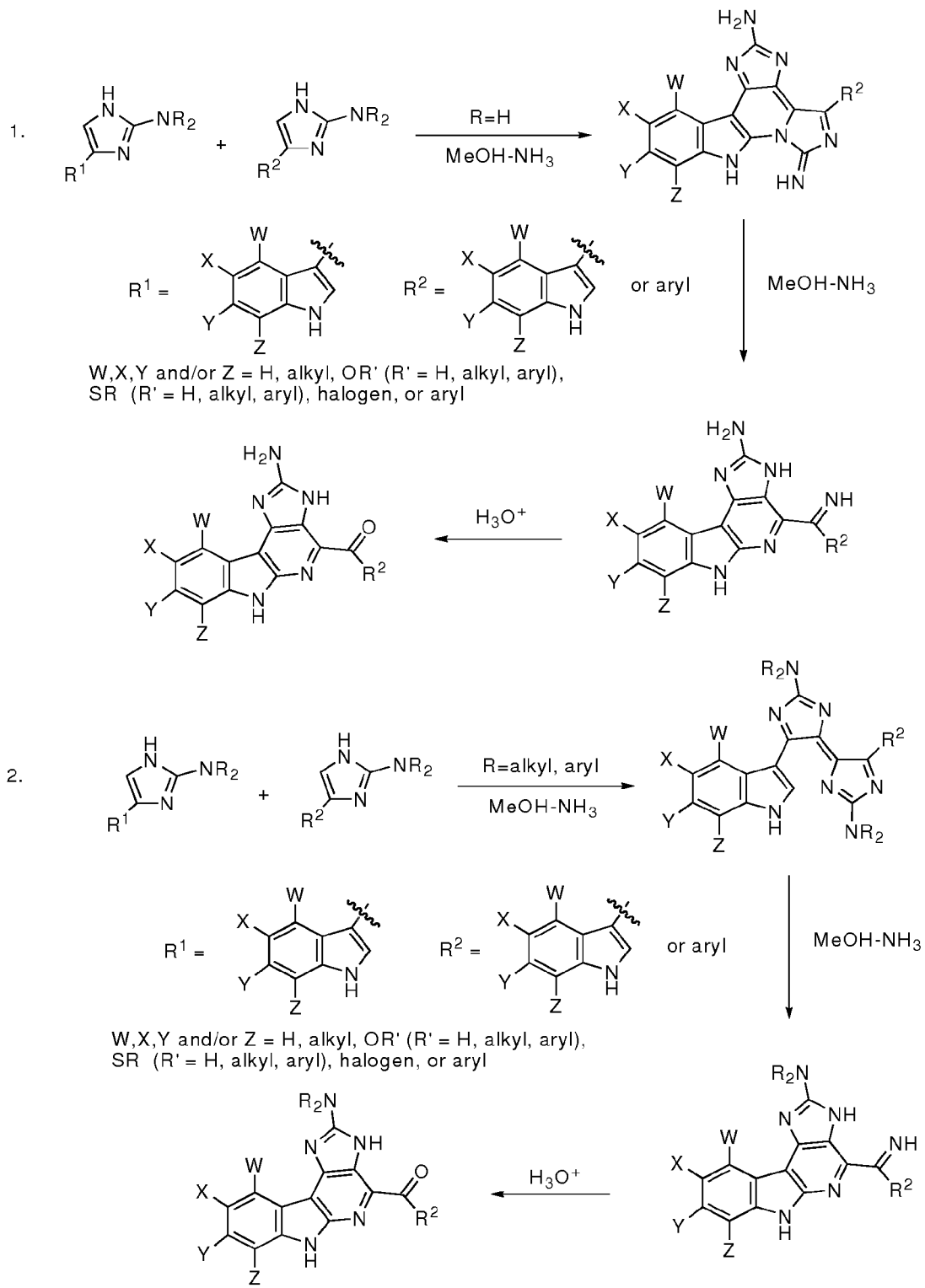
FIG. 7 shows generalized reaction schemes for the preparation of α-carboline analogs.

Referring to FIG. 7(1), in another embodiment of the present invention a more generalized scheme for the synthesis of grossularines-1 or intermediates or derivatives thereof is provided comprising: (1) reacting a first compound

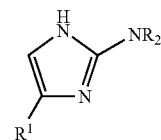

with a second compound

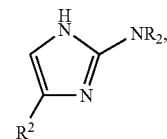

wherein $R^1 =$ 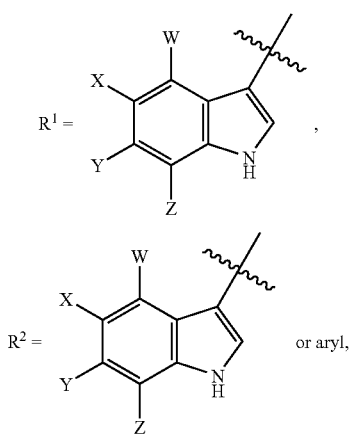, $R^2 =$ 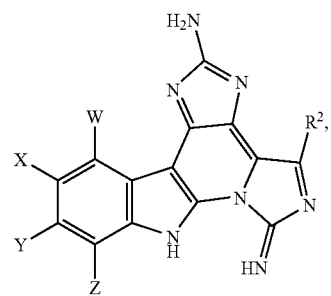 or aryl, and R is hydrogen, and wherein W, X, Y, and Z are each selected from the group consisting of hydrogen, alkyl, halogen, aryl, OR', or SR', wherein R' is hydrogen, alkyl or aryl, to form a third compound having the formula:

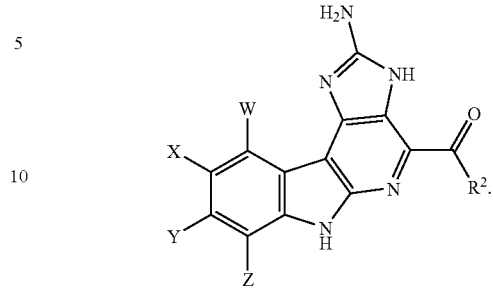

and/or a fourth compound having the formula:

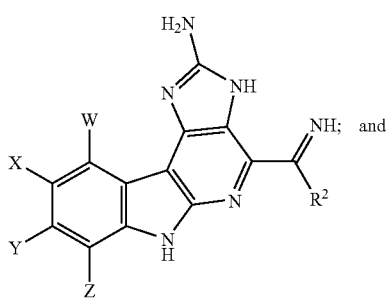

(2) hydrolyzing the fourth compound to form:

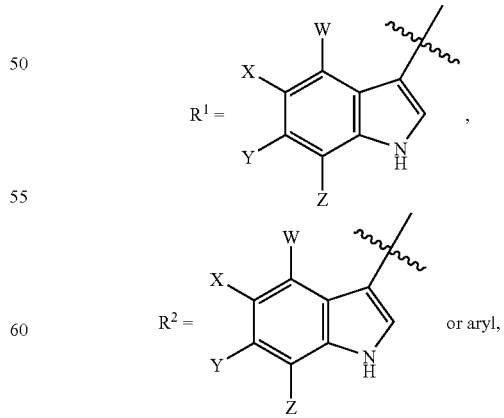

In the present embodiment, reaction step (1) may be performed in the presence of a methanol solution substantially saturated with ammonia. It is observed that the third compound will form the fourth compound after a sufficient time under the same conditions.

Referring to FIG. 7(2), in yet another embodiment of the present invention a second more generalized scheme for the synthesis of grossularines-1 or intermediates or derivatives thereof is provided comprising: (1) reacting a first compound

with a second compound

wherein $R^1 =$ 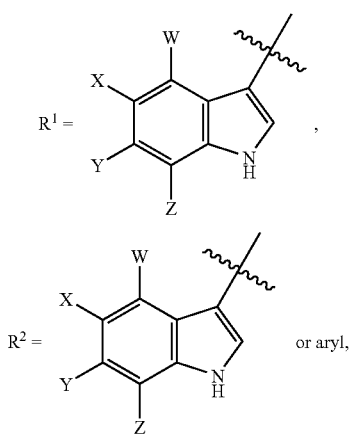, $R^2 =$ 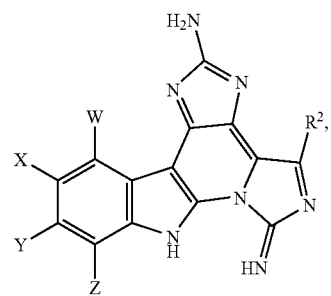 or aryl, and R is alkyl or aryl, and wherein W, X, Y, and Z are each selected from the group consisting of hydrogen, alkyl, halogen, aryl, OR', or SR', wherein R' is hydrogen, alkyl or aryl, to form a third compound having the formula:

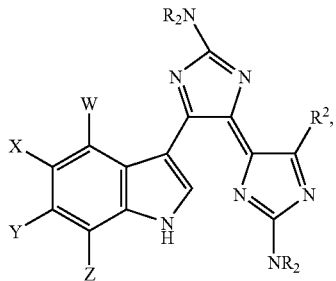

and/or a fourth compound having the formula:

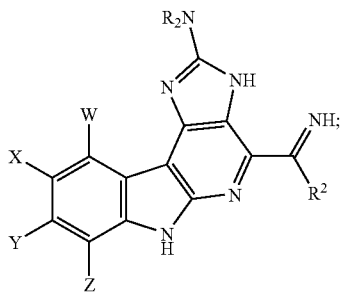

and (2) hydrolyzing the third or fourth compound to form:

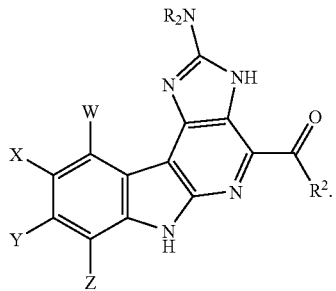

In the present embodiment, reaction step (1) may be performed in the presence of a methanol solution substantially saturated with ammonia. It is observed that the third compound will form the fourth compound after a sufficient time under the same conditions.

In another embodiment grossularine-1 1 analogs may be prepared including: N,N-diethyl-pre-grossularine-1 11, where R=NEt$_2$; N,N-diethyl-grossularine-1 12, where R=NEt$_2$; piperidinyl-pre-grossularine-1 13, where

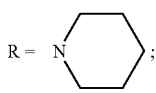

and piperidinyl-grossularine-1 14, where

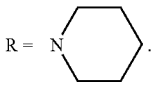

Said analogs are prepared in the same manner as the methods setforth herein except N,N-diethylcyanamide is used instead of N,N-dimethylcyanamide in the condensation steps in the synthesis of N,N-diethyl-pre-grossularine-1 11 and N,N-diethyl-grossularine-1 12, and piperidinylcyanamide is used instead of N,N-dimethylcyanamide in the condensation steps in the synthesis of piperidinyl-pre-grossularine-1 13 and piperidinyl-grossularine-1 14. Yields of 30%-60% have been obtained using said methods.

In addition to the examples or R groups set forth herein, it is also contemplated that other R groups could be used such as those to form a dimer such as a homodimer or a heterodimer with at least any of compounds 1-14 setforth herein.

In another embodiment of the present invention, a method for treating tumors, cancers, neoplastic tissue and other premalignant and nonneoplastic hyperproliferative or hyperplastic disorders is described comprising the use grossularines-1 or derivatives thereof or pharmaceutically acceptable salts or esters thereof, as an as an antitumor agent by inhibiting or preventing the growth of tumors, cancers, neoplastic tissue and other premalignant and nonneoplastic hyperproliferative or hyperplastic disorders. The method may be used to inhibit growth and/or induce cytotoxicity by necrotic or apoptotic mechanisms, or both, in the target cells which are generally hyperproliferative cells including tumors, cancers and neoplastic tissue along with premalignant and non-neoplastic or non-malignant hyperproliferative disorders.

Examples of tumors, cancers and neoplastic tissue that can be treated by the present method include but are not limited to malignant disorders such as breast cancers, osteosarcomas, angiosarcomas, fibrosarcomas and other sarcomas, leukemias, lymphomas, sinus tumors, ovarian, uretal, bladder, prostate and other genitourinary cancers, colon, esophageal and stomach cancers and other gastrointestinal cancers, lung cancer, myelomas, pancreatic cancers, liver cancers, kidney cancers, endocrine cancers, skin cancers, and brain or central and peripheral nervous system tumors, malignant or benign, including gliomas and neuroblastomas.

Examples of pre-malignant and non-malignant hyperproliferative disorders include but are not limited to myelodysplastic disorders, cervical carcinoma-in-situ, familial intestinal polyposes such as Gardner's syndrome, oral leukoplakias, histiocytosis, keloids, hemangiomas, hyperproliferative arterial stenosis, inflammatory arthritis, hyperkeratosis and papulosquamous eruptions including arthritis. Also included are viral induced hyperproliferative diseases such as warts and EBV induced disease such as infectious mononucleosis, scar formation and the like. The method may be employed with any subject known or suspected of carrying or at risk of developing a hyperproliferative disorder.

Treatment of a hyperproliferative disorder refers to methods of killing inhibiting or slowing the growth or increase in size of a body or population of hyperproliferative cell numbers or preventing spread to other anatomical sites as well as reducing the size of a hyperproliferative growth or numbers of hyperproliferative cells. Treatment is not necessarily meant to imply a cure or complete abolition of hyperproliferative growths. A treatment effective amount is an amount effective to result in the killing, the slowing of the rate of growth of hyperproliferative cells the decrease in the size of a body of hyperproliferative cells, and or the reduction in number of hyperproliferative cells.

Formulation and Administration

The active compounds may be formulated for administration in a single pharmaceutical carrier or in separate pharmaceutical carriers for the treatment of a variety of conditions. The carrier must be compatible with any other ingredients in the formulation and must not be deleterious to the patient. The carrier may be a solid or liquid or both and is preferably formulated with the compound as a unit dose formulation, such as a tablet which may contain 0.5% to 95% by weight of the active compound. One or more active compounds may be incorporated into the formulation which may be prepared by any of the known techniques of pharmacy consisting essentially of admixing the components and optionally including one or more accessory ingredients.

The formulations of the present invention are those suitable for oral, rectal, buccal (e.g., sub-ligual), vaginal, parenteral (e.g., subcutaneous, intramuscular, intradermal, or intravenous), topical (both skin and mucosal surfaces, including airway surfaces) and transdermal administration, although the most suitable route in any given case will depend on the nature and severity of the condition being treated and on the nature of the particular active compound being used.

Formulations suitable for oral administration may be presented in discrete units such as capsules cachets, lozenges, or tablets each containing a predetermined amount of the active compound(s), as a powder or granules, as a solution or a suspension in an aqueous or non-aqueous liquid, or as an oil-in-water or water-in-oil emulsion or a liposomal formulation. Such formulations may be prepared by any suitable method of pharmacy which includes the step of bringing into association the active compound and a suitable carrier (which may contain one or more accessory ingredients). In general, formulations are prepared by uniformly and intimately admixing the active compound with a liquid or finely divided solid carrier, or both, and then if necessary shaping the resulting mixture. For example a tablet may be prepared by compressing or molding a powder or granules containing the active compound(s), optionally with one or more accessory ingredients. Other delivery formulations may suggest themselves to one skilled in the art.

The therapeutically effective dosages of any one active ingredient will vary somewhat from compound to compound, patient to patient, and will depend upon factors such as the condition of the patient and the route of delivery. Such dosages can be determined in accordance with known pharmacological procedures in light of the disclosure herein.

EXAMPLES

The following examples are provided to exemplify certain particular features of working embodiments of the present invention. The scope of the present invention should not be limited to those features exemplified.

Example 1

Figure 17:
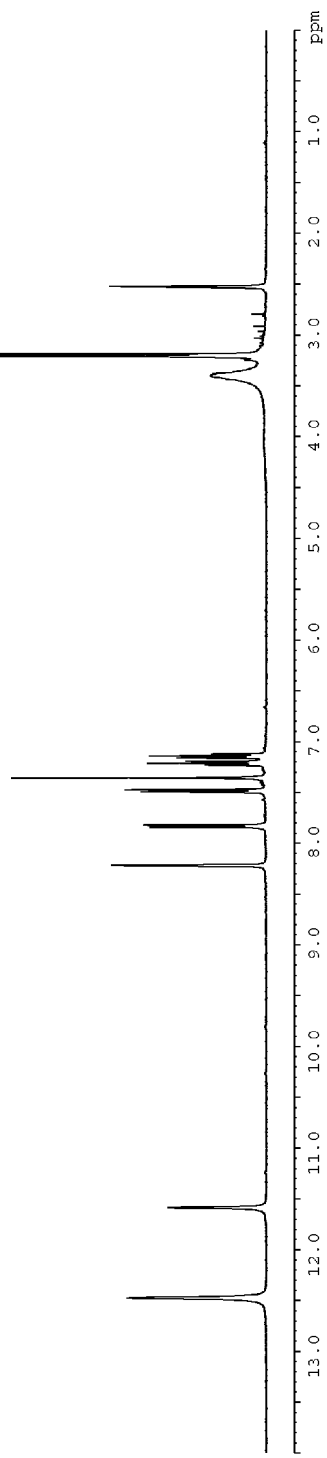
FIGS. 17 and 18 show spectral data for 2-dimethylamino-4-(3-indolyl)imidazole 5.
Figure 17:
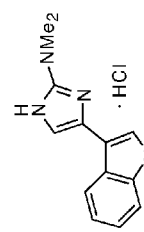
Figure 18:
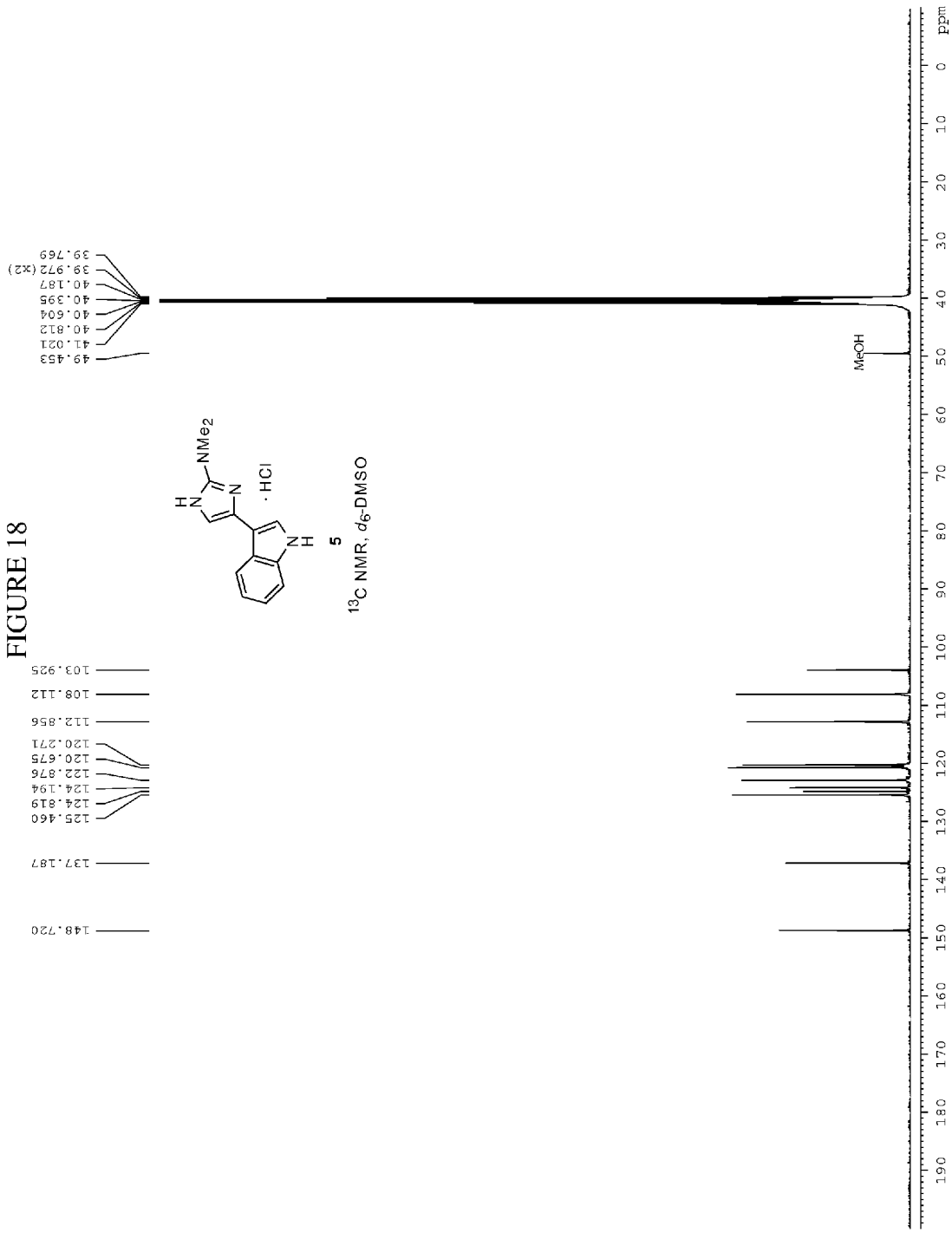

This example describes the synthesis of the hydrochloride salt of indole aminoimidazole 5 of FIG. 4, 2-dimethylamino-4-(3-indolyl)imidazole 5.HCl. A mixture of oxotryptamine 3.HCl (0.7 g, 3.3 mmol) and dimethylcyanamide (4 mL, 50 mmol) was stirred under nitrogen at 135° C. for 24 hours in sealed tube. The resulting residue was washed with ether and triturated with ethanol which afforded 2-dimethylamino-4-(3-indolyl)imidazole 5 as the hydrochloride salt; colorless solid (0.7 g 75%). Referring to FIGS. 17 and 18, Compound 5.HCl: $^1$H NMR (300 MHz, DMSO-$d_6$) δ 12.45 (s, 2H), 11.56 (s, 1H), 8.19 (d, J=2.0 Hz, 1H), 7.80 (d, J=7.7 Hz, 1H), 7.45 (d, J=8.0 Hz, 1H), 7.33 (s, 1H), 7.18 (bt, J=7.4 Hz, 1H), 7.11 (bt, J=7.3 Hz, 1H), 3.17 (s, 6H); $^{13}$C NMR (100 MHz, DMSO-$d_6$) δ 148.7 (s), 137.2 (s), 125.5 (d), 124.8 (s), 124.2 (s), 122.9 (d), 120.7 (d), 120.3 (d), 112.9 (d), 108.1 (d), 103.9 (s), 40.0 (qx2); HRFABMS calcd for $C_{13}H_{15}N_4$ 227.1297, found 227.1300.

Example 2

Figure 19:
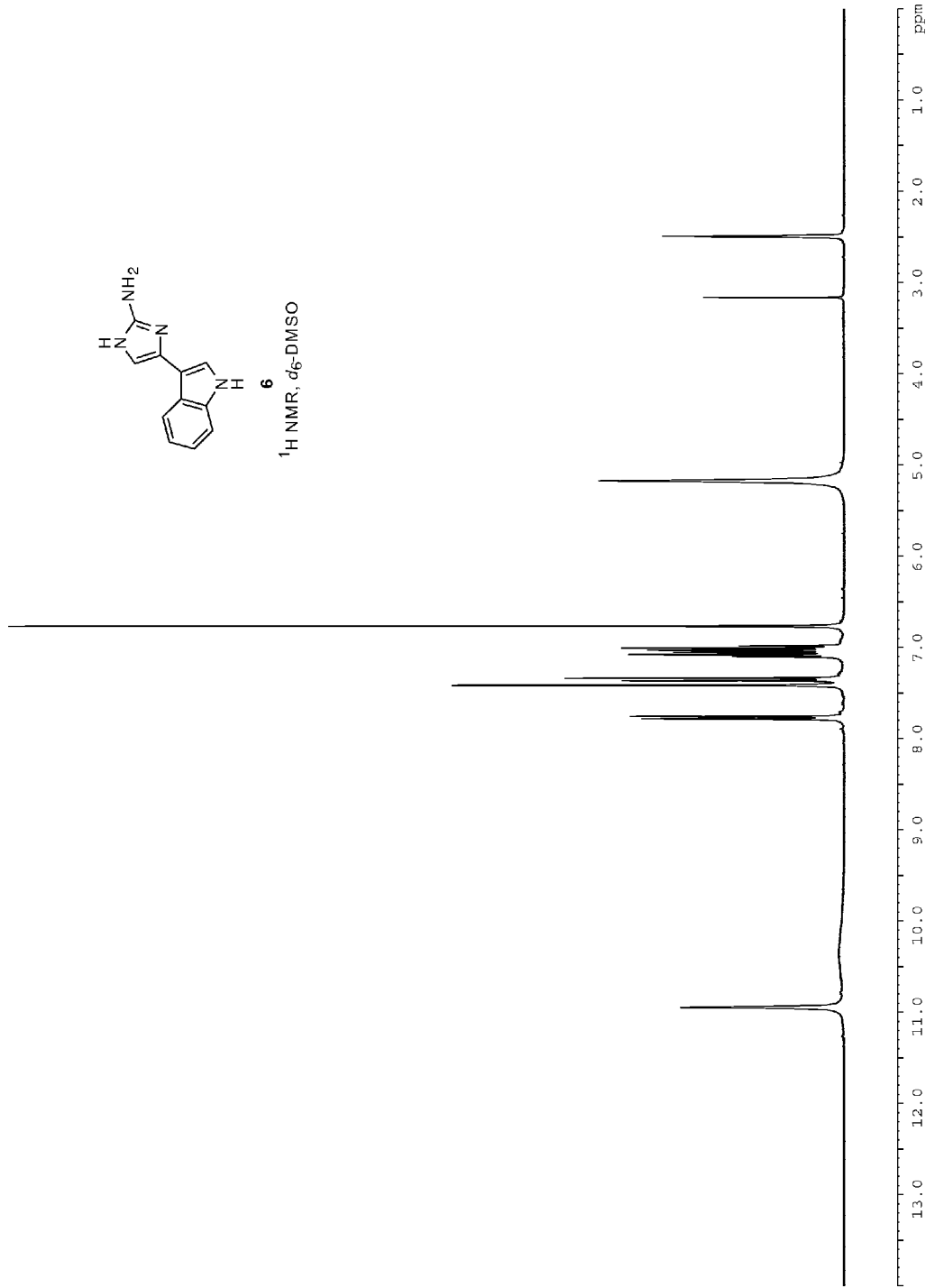
FIGS. 19 and 20 show spectral data for 2-amino-4-(3-indolyl)imidazole 6.
Figure 20:
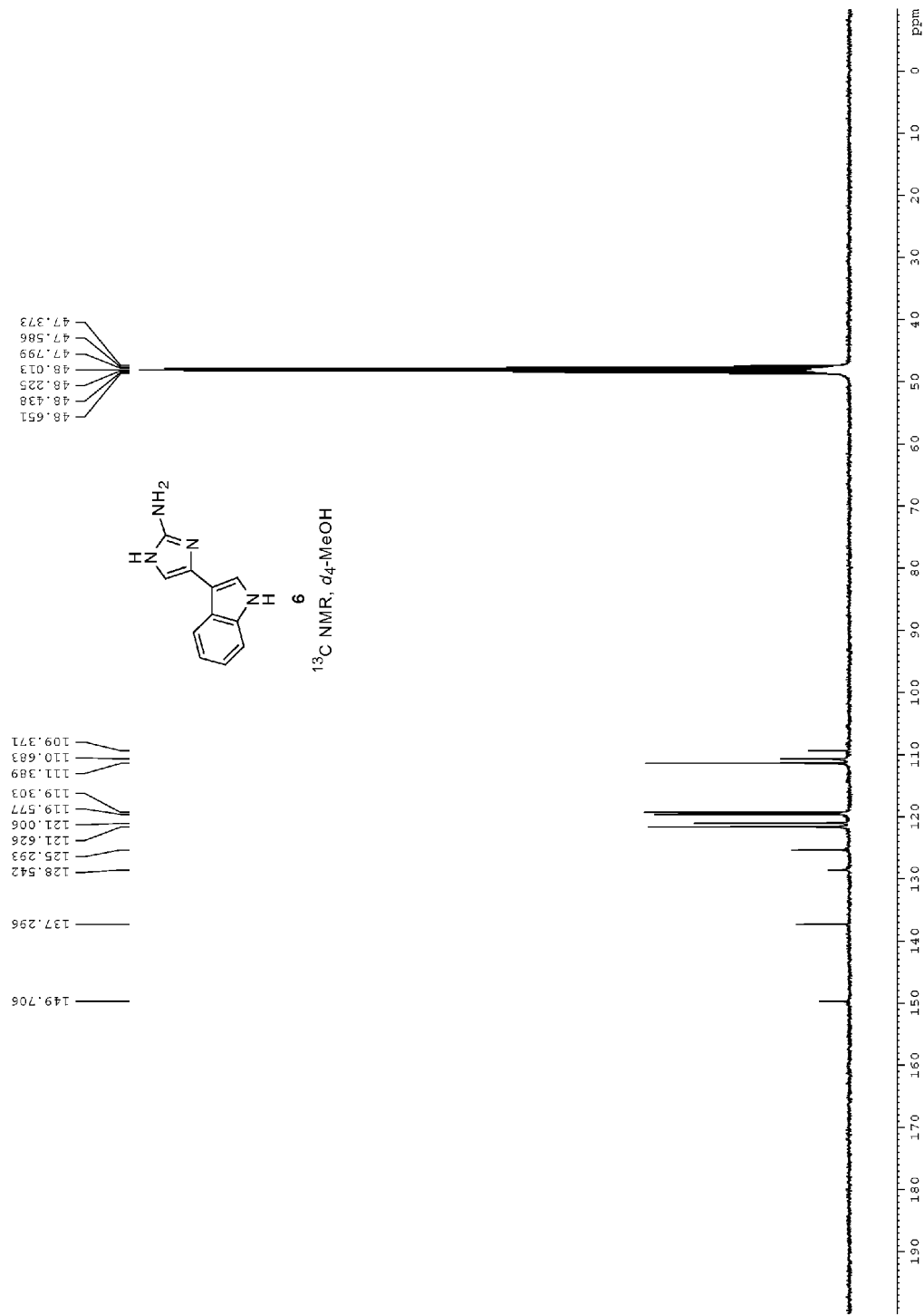

This example describes the synthesis of indole aminoimidazole 6 of FIG. 4, 2-amino-4-(3-indolyl)imidazole 6. A mixture of oxotryptamine 3.HCl (0.3 g, 1.4 mmol) and cyanamide (0.6 g, 14 mmol) was heated under nitrogen at 110° C. for 16 hours in sealed tube. The reaction mixture was allow to cool to 25° C. and the resulting residue was washed with ether. Flash silica gel chromatography ($CH_2Cl_2$/MeOH(NH$_3$), 17:3) afforded 2-amino-4-(3-indolyl)imidazole 6 as a colorless solid. Referring to FIGS. 19 and 20, Compound 6: $^1$H NMR (300 MHz, DMSO-$d_6$) δ 10.95 (s, 1H), 10.42 (br, 1H), 7.77 (bd, J=7.8 Hz, 1H), 7.41 (d, J=2.4 Hz, 1H), 7.35 (bd, J=7.8 Hz, 1H), 7.08 (td, J=7.8, 1.2 Hz, 1H), 7.01 (td, J=7.8, 1.2 Hz, 1H), 6.77 (s, 1H), 5.17 (s, 2H); $^{13}$C NMR (100 MHz, DMSO-$d_6$) δ 150.1 (s), 137.3 (s), 129.2 (s), 125.4 (s), 121.9 (d), 121.5 (d), 120.8 (d), 119.6 (d), 112.3 (d), 111.0 (s), 110.6 (d); HRFABMS calcd for $C_{11}H_{11}N_4$ 199.0984, found 199.0987.

Example 3

Figure 21:
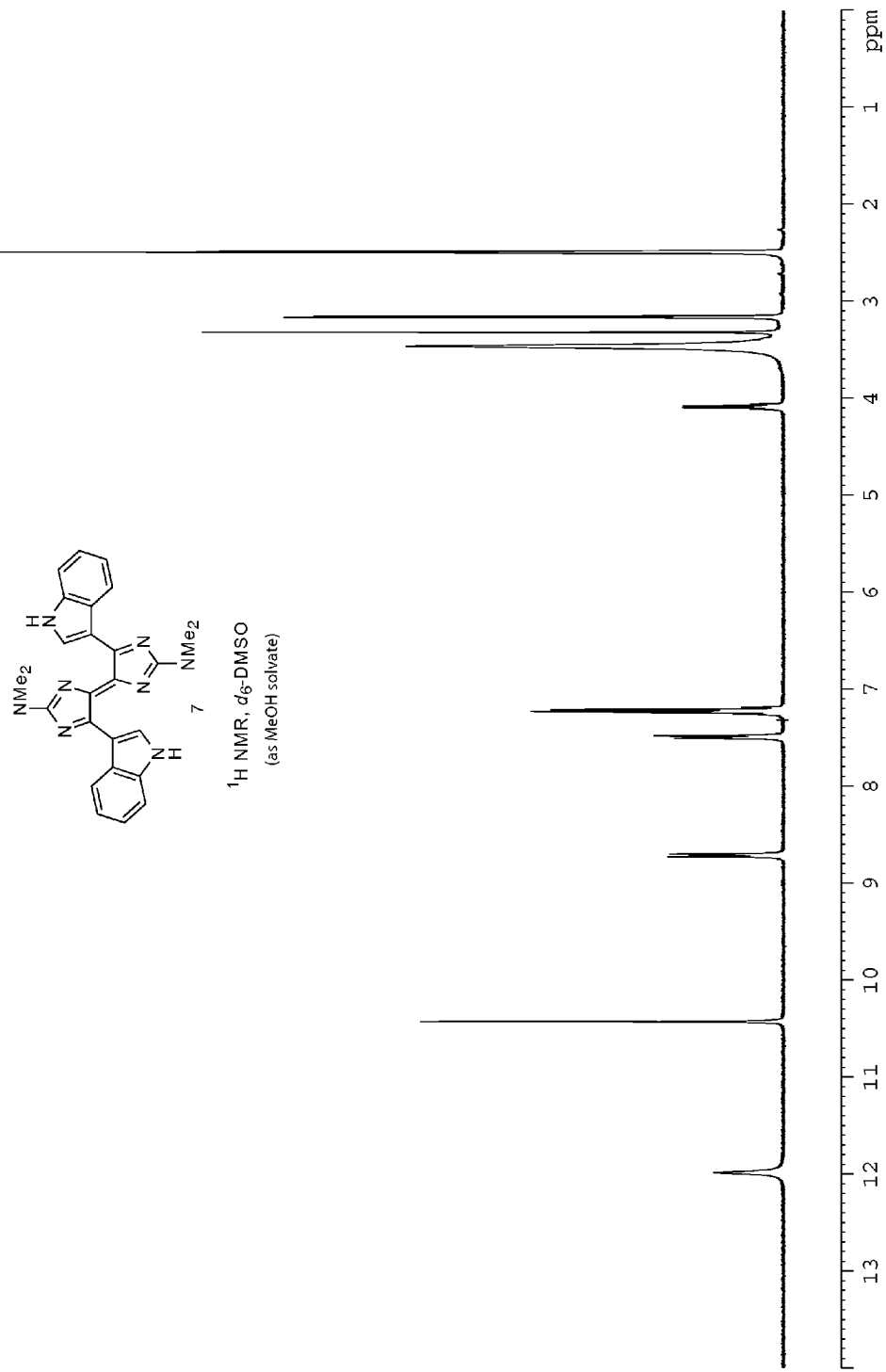
FIGS. 21 and 22 show spectral data for dimer 7.
Figure 22:
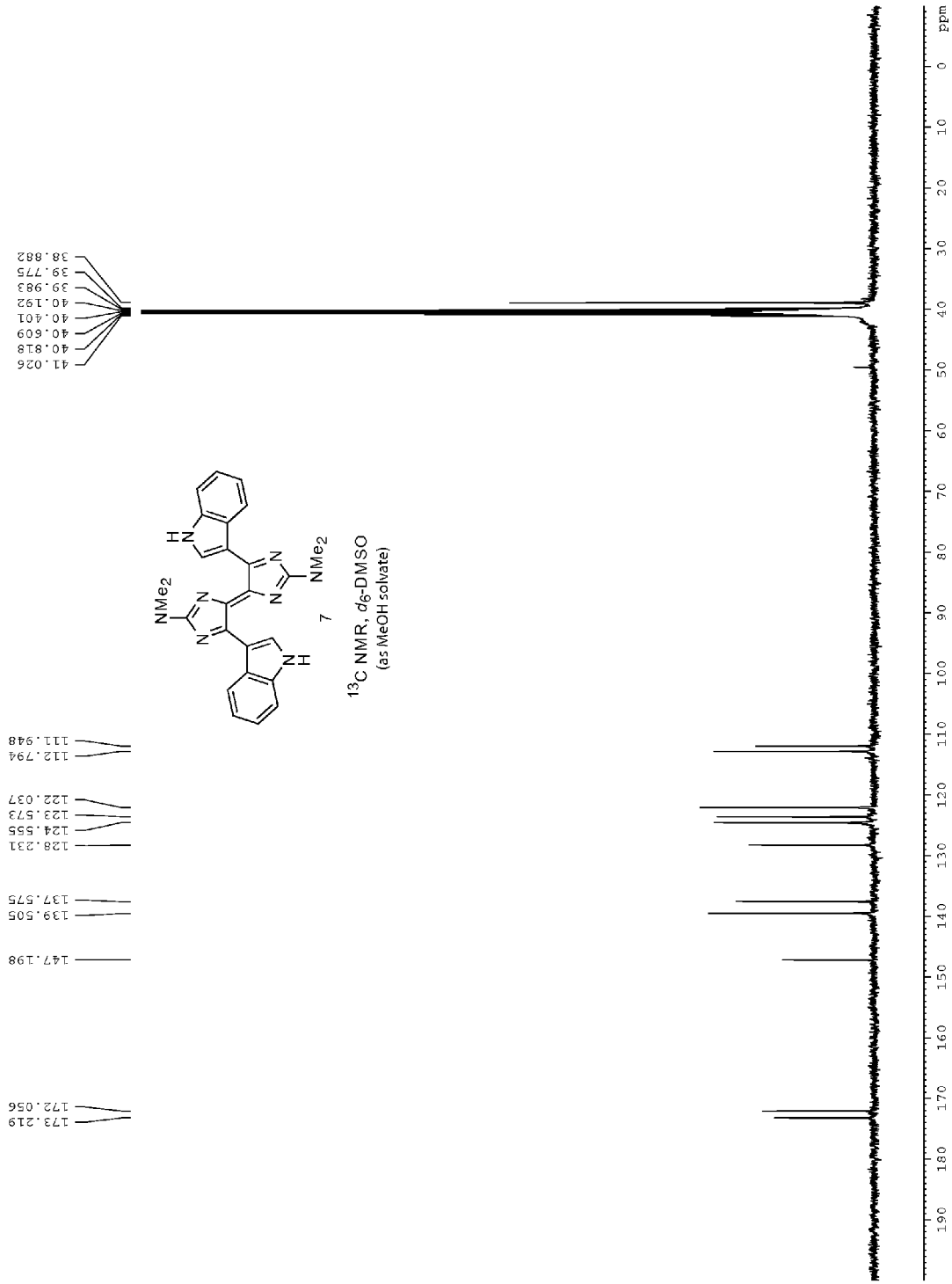
Figure 23:
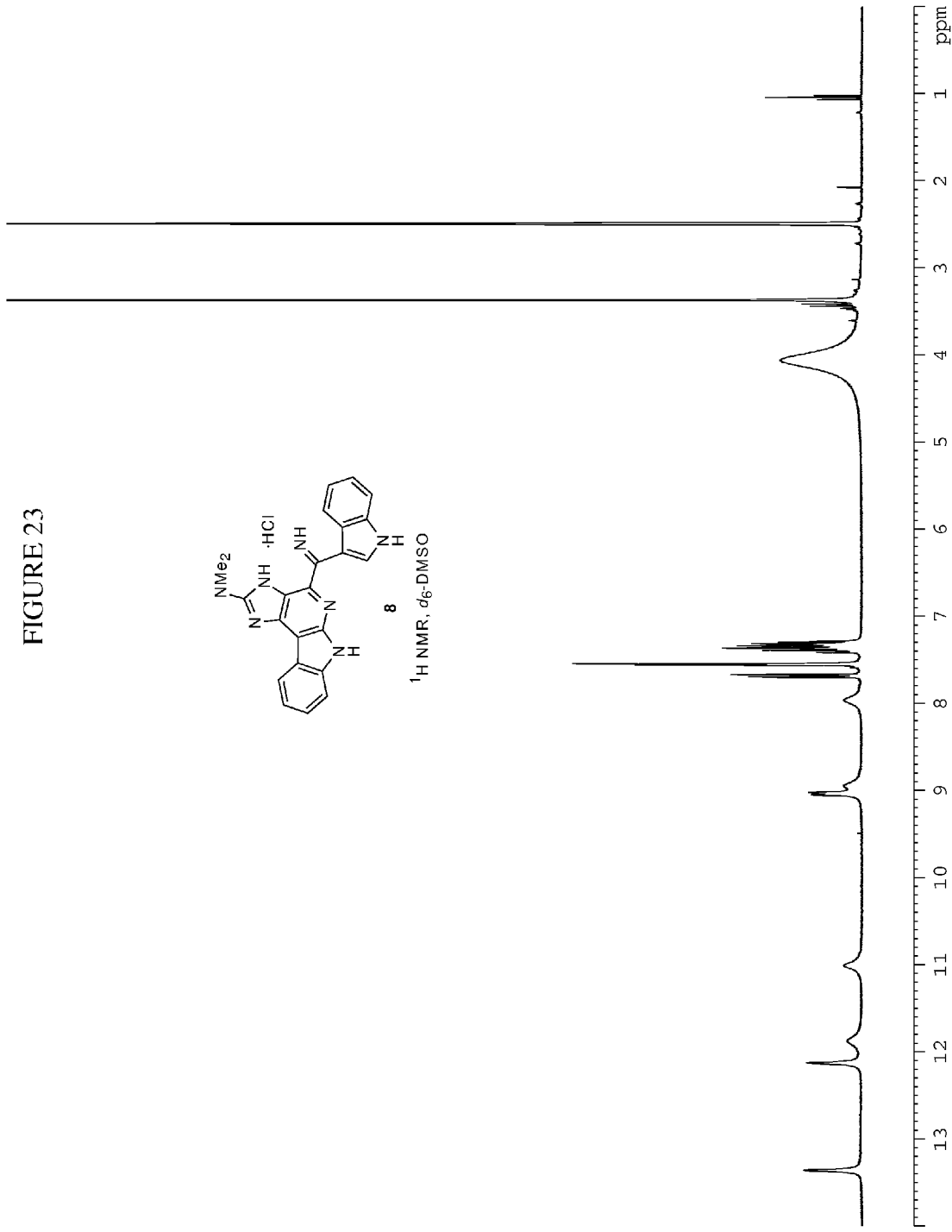
FIGS. 23-25 show spectral data for α-carboline imine 8.
Figure 24:
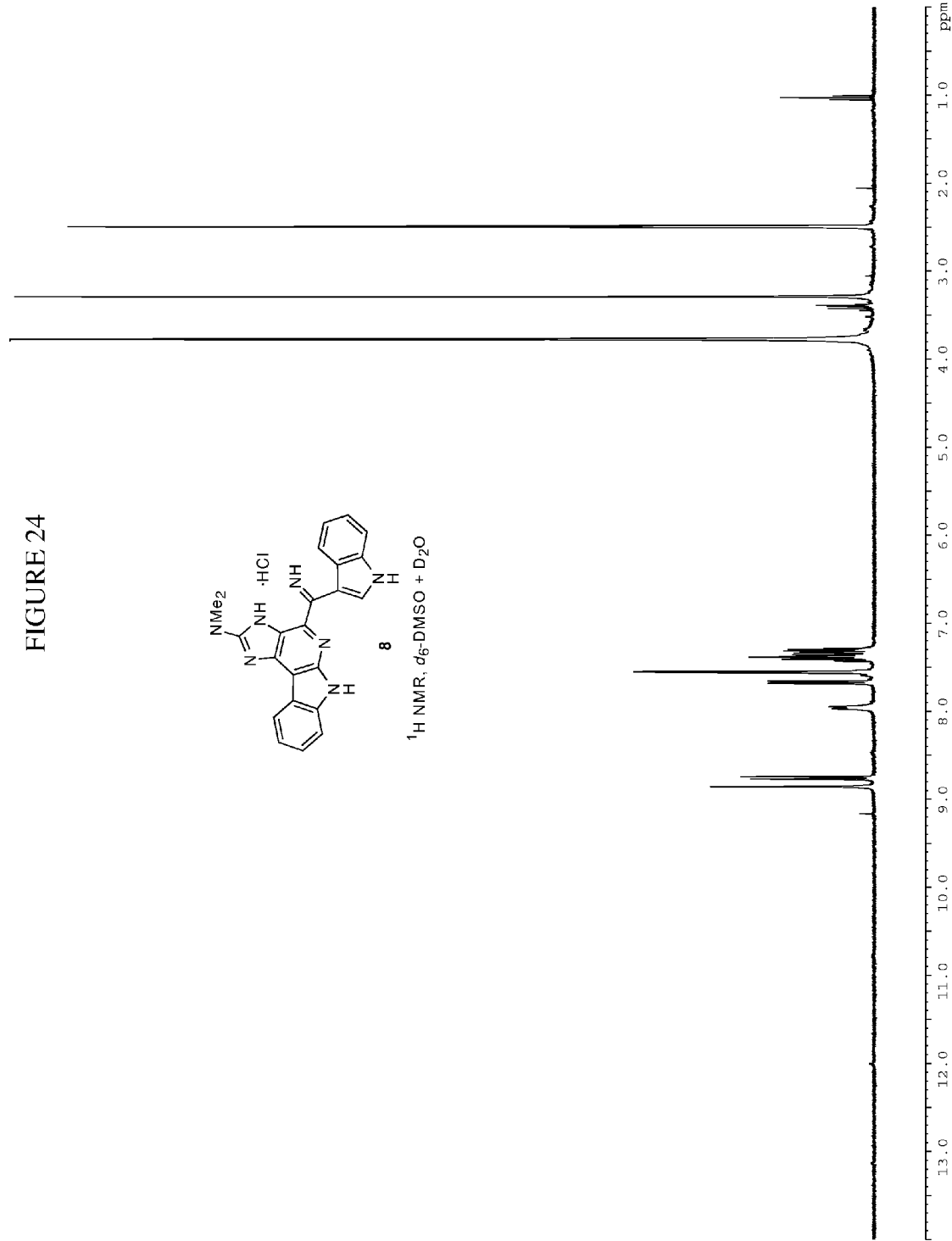
Figure 25:
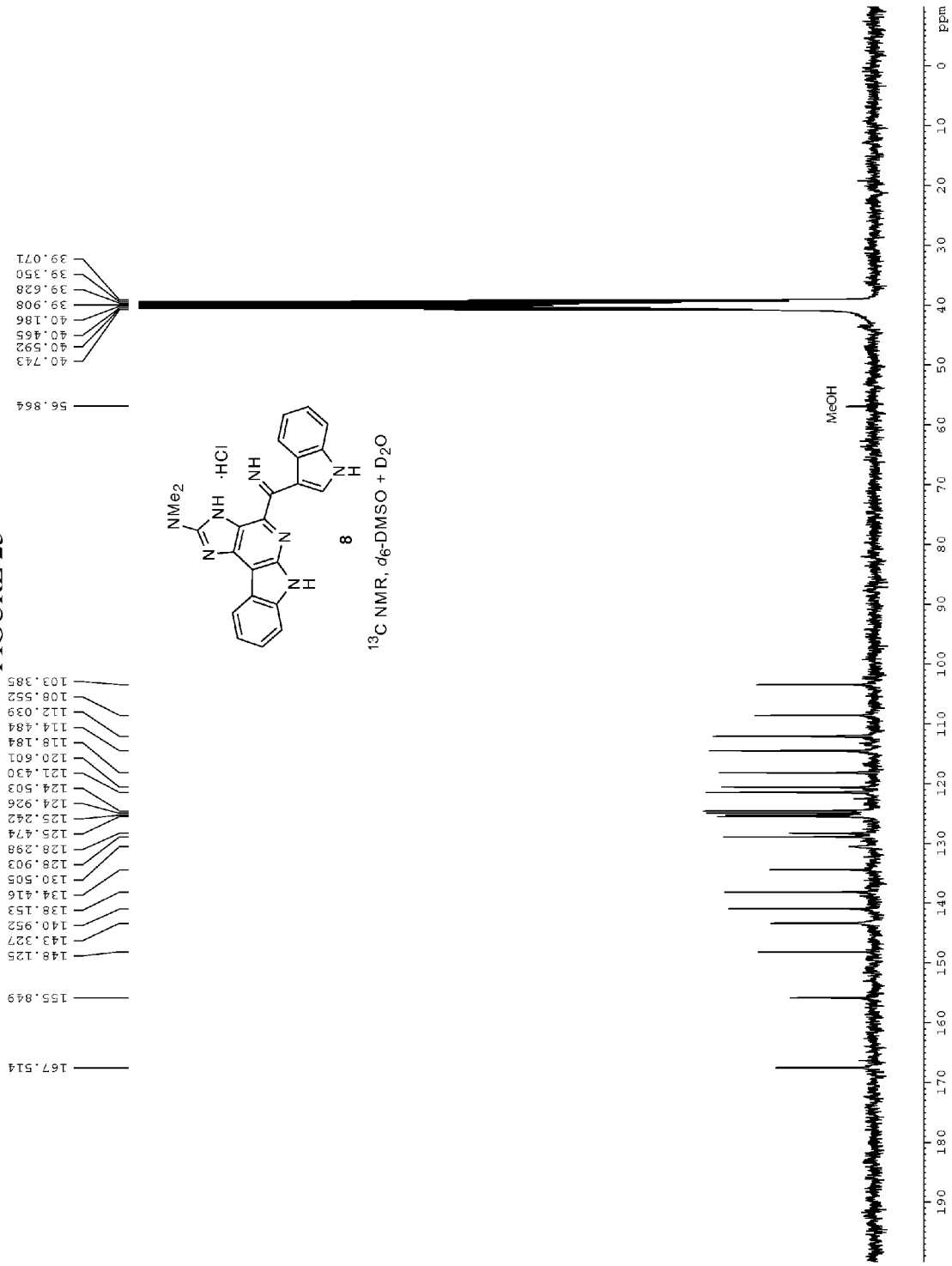

This example describes the synthesis of compounds 7 and 8 of FIG. 5. A solution of 2-dimethylamino-4-(3-indolyl)imidazole 5.HCl (0.2 g, 0.76 mmol) in 40 mL of methanol saturated with ammonia (MeOH, sat. NH$_3$) was allow to stir in the presence of air at 25° C. for 1 day during which time compound 7 precipitated from the solution as a dark solid and was collected by filtration. Resubjection of 7 to an ammonia saturated methanol solution in air for 7 days at 25° C. produced compound 8 as a orange solid after concentration of the reaction mixture in vacuo followed by Flash silica gel chromatography ($CH_2Cl_2$/MeOH(NH$_3$), 19:1). The yield of compound 8 was 60%. Referring to FIGS. 21 and 22, Compound 7: $^1$H NMR (300 MHz, DMSO-$d_6$) δ 11.98 (bs, 2H), 10.43 (s, 2H), 8.72 (m, 2H), 7.49 (m, 2H), 7.22 (m, 4H), 3.46 (bs, 6H); $^{13}$CNMR (100 MHz, DMSO-$d_6$) δ 173.2 (sx2), 172.1 (sx2), 147.2 (sx2), 139.5 (dx2), 137.6 (sx2), 128.2 (sx2), 124.6 (dx2), 123.6 (dx2), 122.0 (dx2), 112.8 (dx2), 111.9 (sx2), 38.9 (qx4); HRFABMS calcd for $C_{26}H_{25}N_8$ 449.2202, found 449.2178. Referring to FIGS. 23-25, Compound 8: $^1$H NMR (300 MHz, DMSO-$d_6$) δ 13.36 (s, 1H), 12.13 (s, 1H), 11.88 (bs, 1H), 11.00 (bs, 1H), 9.03 (d, J=7.7 Hz, 1H), 8.94 (bs, 1H), 7.96 (bs, 1H), 7.68 (dm, J=7.7 Hz, 1H), 7.55 (m, 2H), 7.42-7.28 (m, 3H), 3.37 (s, 6H); $^{13}$C NMR (100 MHz, DMSO-$d_6$+ $D_2O$) δ 167.5 (s), 155.8 (s), 148.1 (s), 143.3 (d), 141.0 (s), 138.2 (s), 134.4 (s), 130.5 (s), 128.9 (d), 128.3 (d), 125.5 (d), 125.2 (s), 124.9 (d), 124.5 (d), 121.4 (d), 120.6 (d), 118.2 (s), 114.5 (d), 112.0 (d), 108.6 (s), 103.4 (s), 40.4 (qx2); HRFABMS calcd for $C_{23}H_{20}N_7$ 394.1780, found 394.1784.

Example 4

Figure 13:
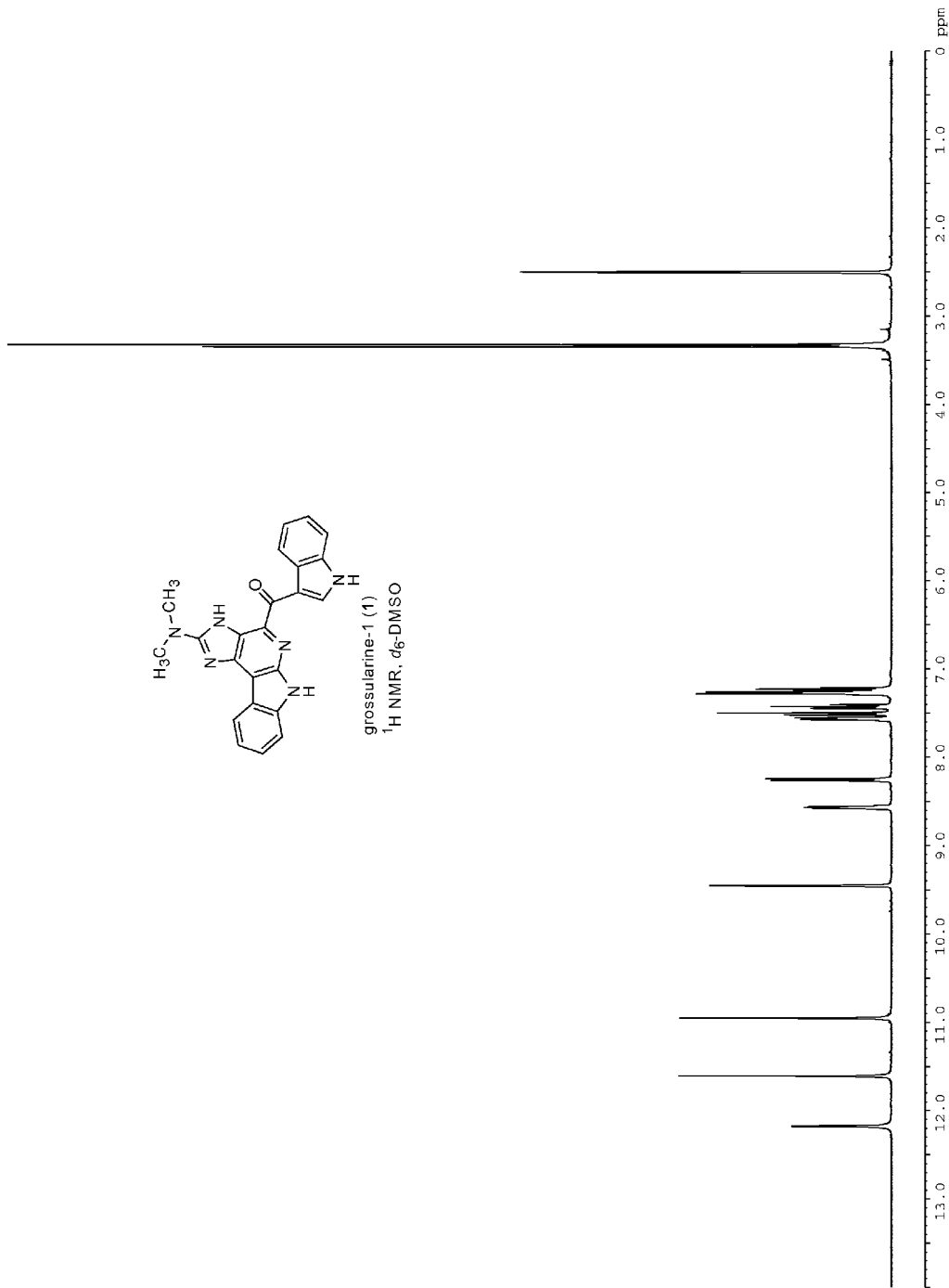
FIGS. 13 and 14 show spectral data for grossularine-1 1.
Figure 14:
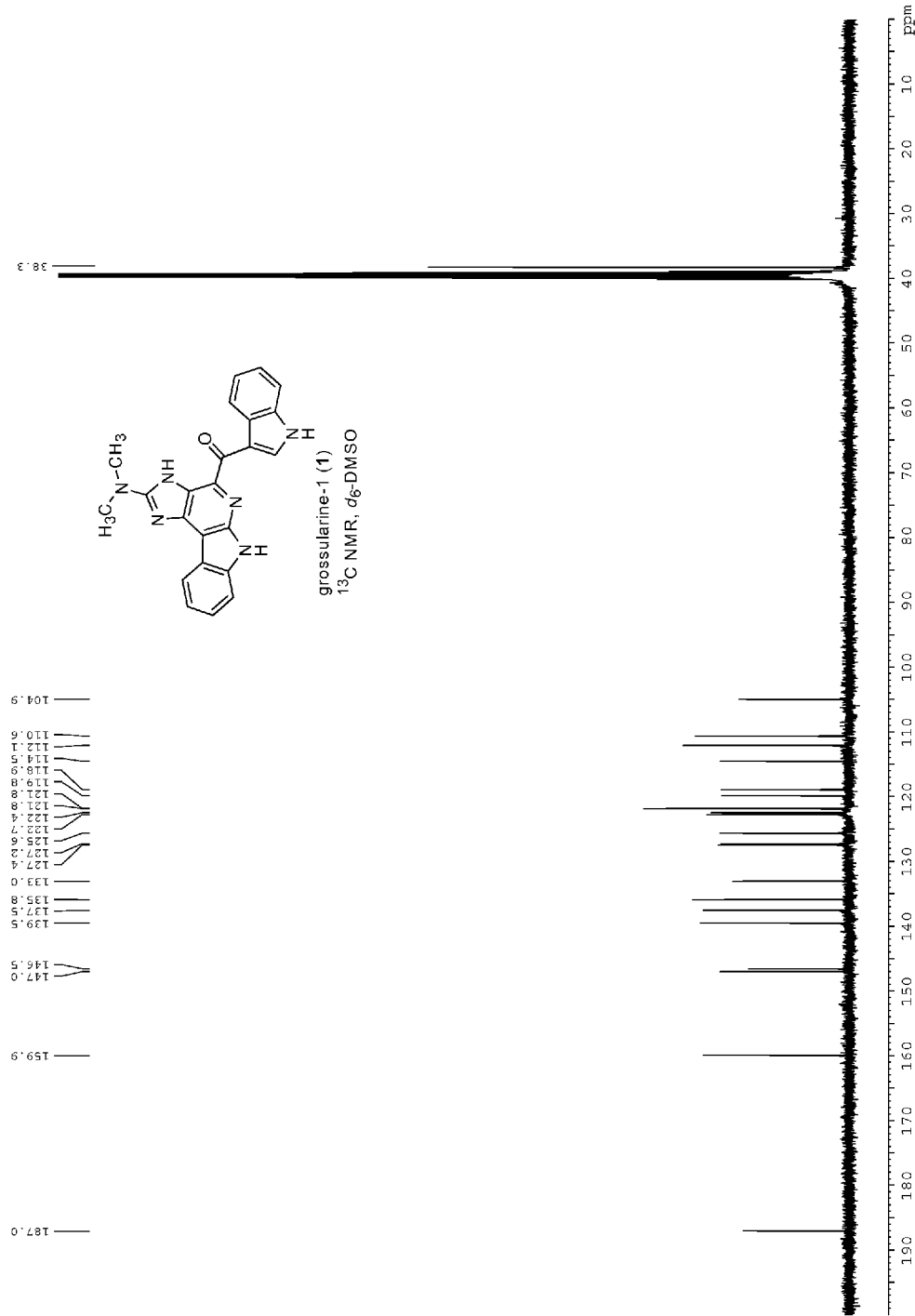

This example describes the synthesis of grossularine-1 1 of FIG. 5. A solution of compound 8 (30 mg, 0.076 mmol) in 40 mL of EtOH-6N HCl (1:1) was stirred at 80° C. for 12 hours in sealed tube. Filtration of the reaction mixture afforded grossularine-1 1.HCl as a yellow solid. The free base of grossularine-1 1 was obtained via neutralization with MeOH (sat. $NH_3$) followed by Flash silica gel chromatography ($CH_2Cl_2$/acetone 19:1). All spectral data of synthetic grossularine-1 1 were consistent with data reported for the natural product. Referring to FIGS. 13 and 14, Compound 1.HCl: $^1$H NMR (300 MHz, DMSO-$d_6$) δ 12.44 (bs, 1H), 12.28 (br, 1H), 12.10 (br, 1H), 9.20 (bs, 1H), 8.89 (br, 1H), 8.52-8.49 (m, 1H), 7.62-7.53 (m, 3H), 7.36-7.27 (m, 3H); Compound 1: $^1$H NMR (300 MHz, DMSO-$d_6$) δ 12.16 (s, 1H), 11.60 (s, 1H), 10.94 (s, 1H), 9.44 (d, J=3.0 Hz, 1H), 8.57-8.54 (m, 1H), 8.24 (d, J=7.6 Hz, 1H), 7.56-7.54 (m, 1H), 7.50 bd, J=8.0 Hz, 1H), 7.42 (bt, J=7.6 Hz, 1H), 7.28-7.24 (m, 2H), 7.22 (bt, J=7.5 Hz, 1H), 3.31 (s, 6H); $^{13}$C NMR (100 MHz, DMSO-$d_6$) δ 187.0 (s), 159.9 (s), 147.0 (s), 146.6 (s), 139.5 (s), 137. (d), 135.9 (s), 133. (s), 127. (s), 127.3 (s), 125.7 (d), 122.7 (d), 122.5 (d), 121.83 (d), 121.80 (d), 119.8 (s), 118.9 (d), 114.5 (s), 112.1 (d), 110.6 (d), 105.0 (s), 38.3 (qx2); HRFABMS calcd for $C_{23}H_{19}ON_6$ 395.1620, found 395.1590.

Example 5

Figure 26:
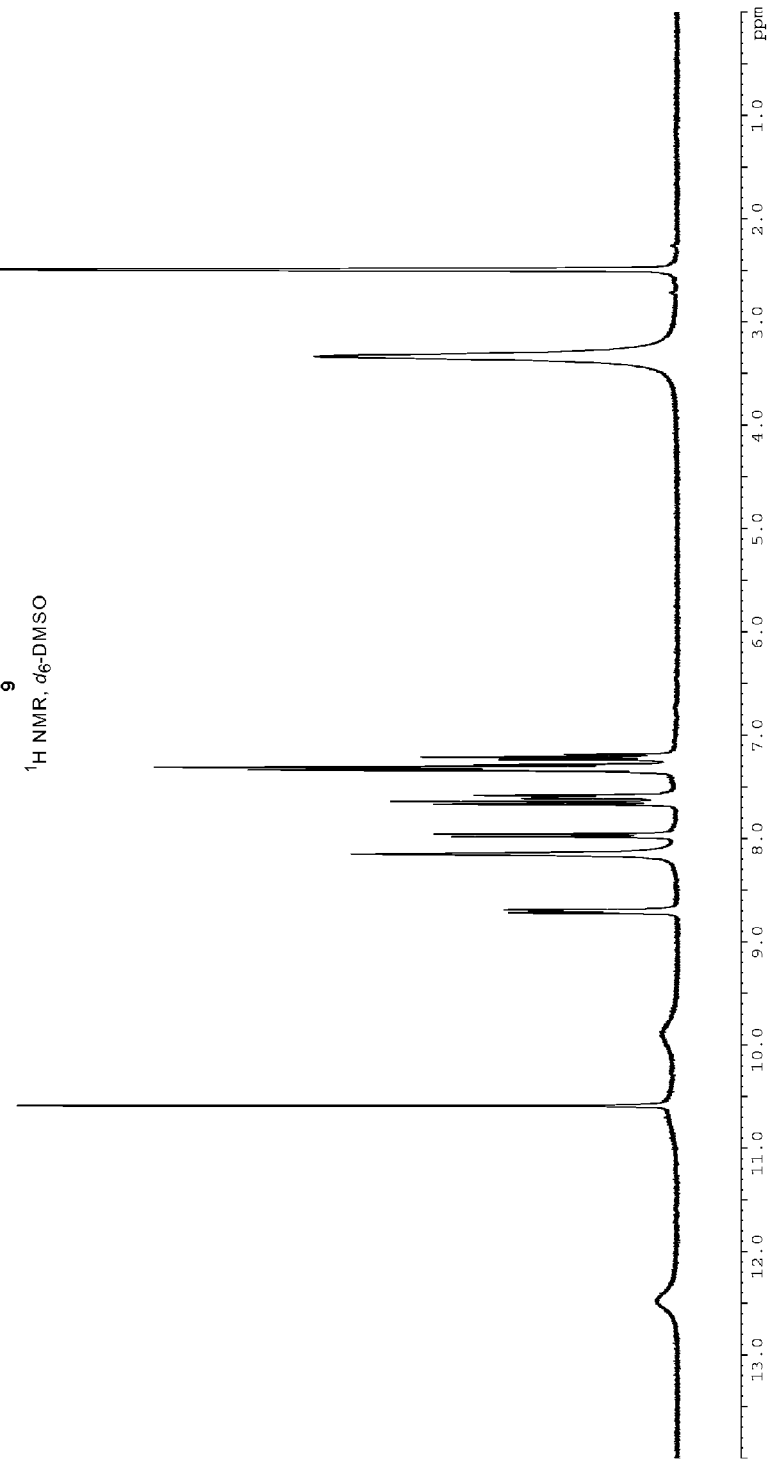
FIGS. 26 and 27 show spectral data for dimer 9.
Figure 27:
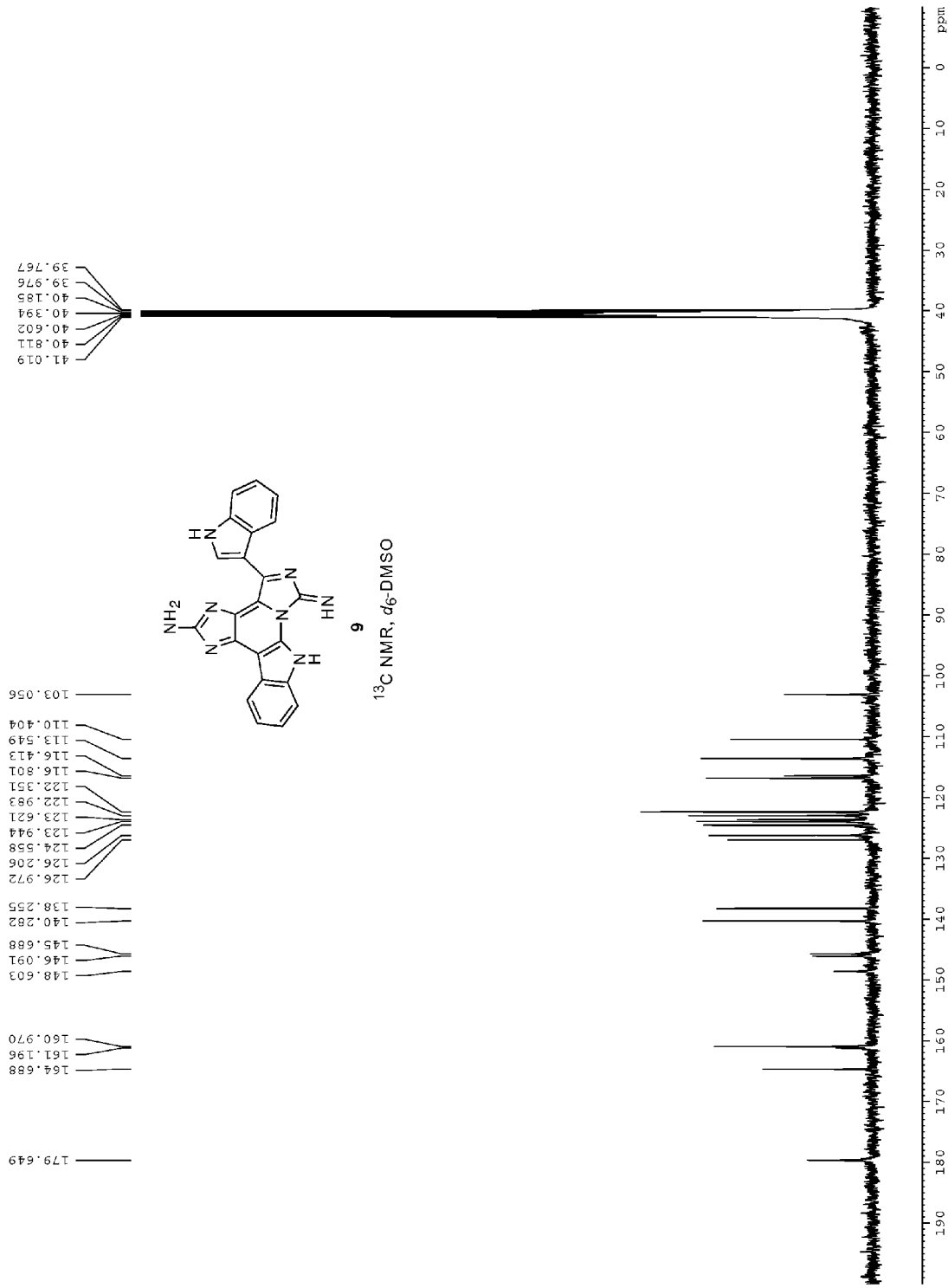
Figure 28:
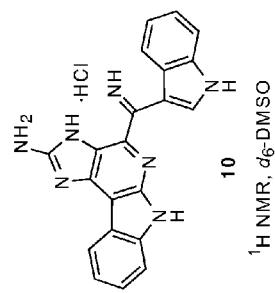
FIGS. 28-30 show spectral data for imine 10.
Figure 28:
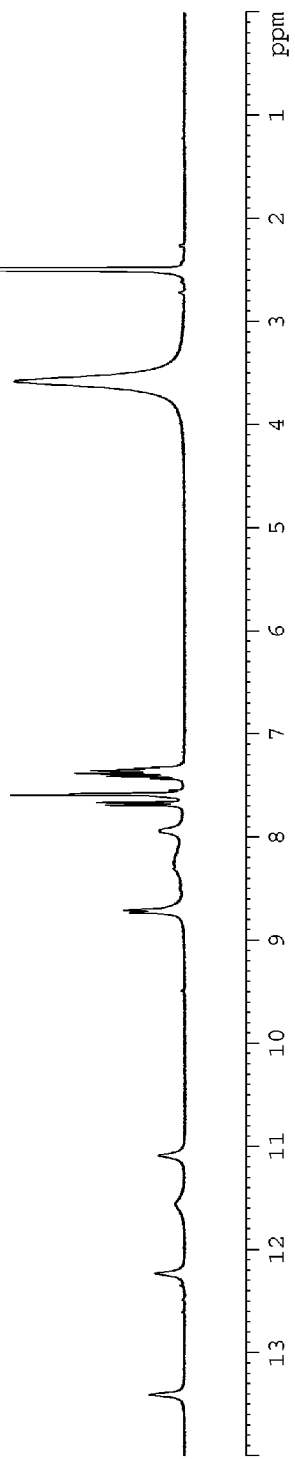
Figure 29:
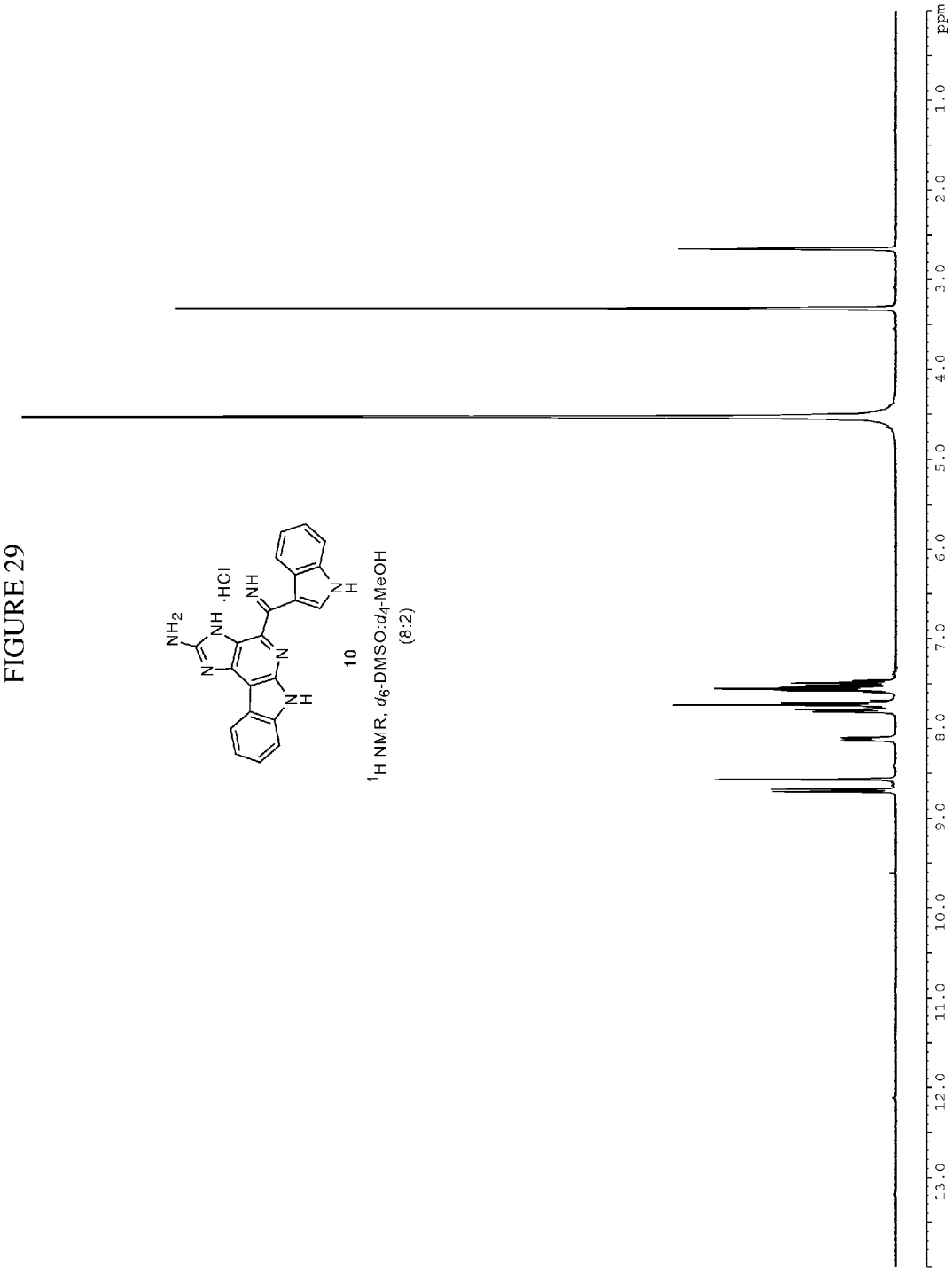
Figure 30:
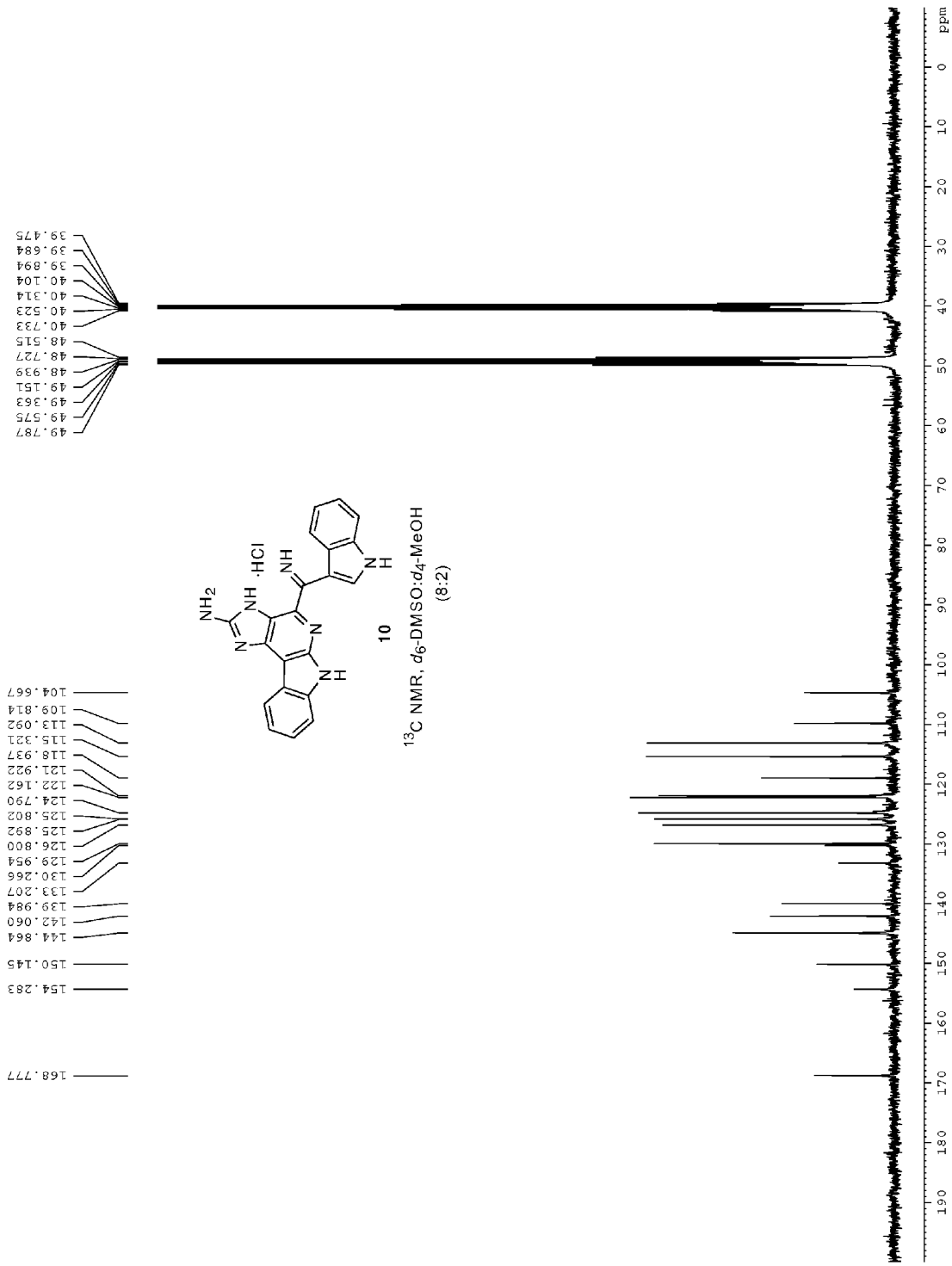

This example describes the synthesis of compounds 9 and 10 of FIG. 6. A solution of 2-amino-4-(3-indolyl)imidazole 6 (0.1 g, 0.5 mmol) in 40 mL of MeOH (sat. $NH_3$) was stirred at 25° C. for 48 hours in the presence of air. Filtration of the resulting precipitate afforded 9 as a dark solid. Resubjection of 9 (50 mg, 0.13 mmol) in 40 mL MeOH (sat. $NH_3$) for 5 days in the presence of air followed by solvent removal in vacuo and Flash silica gel chromatography of the resulting residue [($CH_2CL_2$/MeOH($NH_3$) 9:1] produced 10 as an yellow-orange solid in 60% yield. Referring to FIGS. 26 and 27, Compound 9: $^1$H NMR (300 MHz, DMSO-$d_6$) δ 12.47 (bs, 1H), 10.62 (br, 1H), 10.59 (s, 1H), 9.87 (bs, 1H), 8.71 (m, 1H), 8.15 (bs, 2H), 7.97 (d, J=7.4 Hz, 1H), 7.66 (d, J=7.9 Hz, 1H), 7.60 (m, 1H), 7.36-7.29 (m, 3H), 7.21 (bt, J=7.5 Hz, 1H); $^{13}$C NMR (100 MHz, DMSO-$d_6$) δ 178.8 (s), 163.8 (s), 160.4 (s), 160.1 (s), 147.7 (s), 145.2 (s), 144.8 (s), 139.4 (d), 137.4 (s), 126.1 (s), 125.3 (d), 123.7 (d), 123.1 (d), 122.7 (s), 122.1 (d), 121.5 (d), 121.47 (d), 115.9 (d), 115.5 (s), 112.7 (d), 109.5 (s), 102.2 (s); HRFABMS calcd for $C_{22}H_{15}N_8$ 391.1420, found 391.1413. Referring to FIGS. 28-30, Compound 10; $^1$H NMR (300 MHz, $CD_3OD$/DMSO-$d_6$ 8:2) δ 8.69 (d, J=7.9 Hz, 1H), 8.56 (s, 1H), 8.13-8.10 (m, 1H), 7.82-7.78 (m, 1H), 7.77-7.69 (m, 2H), 7.60-7.46 (m, 3H); $^{13}$C NMR (100 MHz, $CD_3OD$/DMSO-$d_6$, 8:2) δ 167.8 (s), 153.4 (s), 149.2 (s), 143.9 (d), 141.1 (s), 139.1 (s), 132.3 (s), 129.3 (s), 129.0 (s & d), 125.9 (d), 125.0 (s), 124.9 (d), 123.9 (d), 121.2 (s), 121.0 (d), 118.0 (s), 114.4 (d), 112.2 (d), 108.9 (s), 103.7 (s); HRFABMS calcd for $C_{21}H_{16}N_7$ 366.1467, found 366.1473.

Example 6

Figure 15:
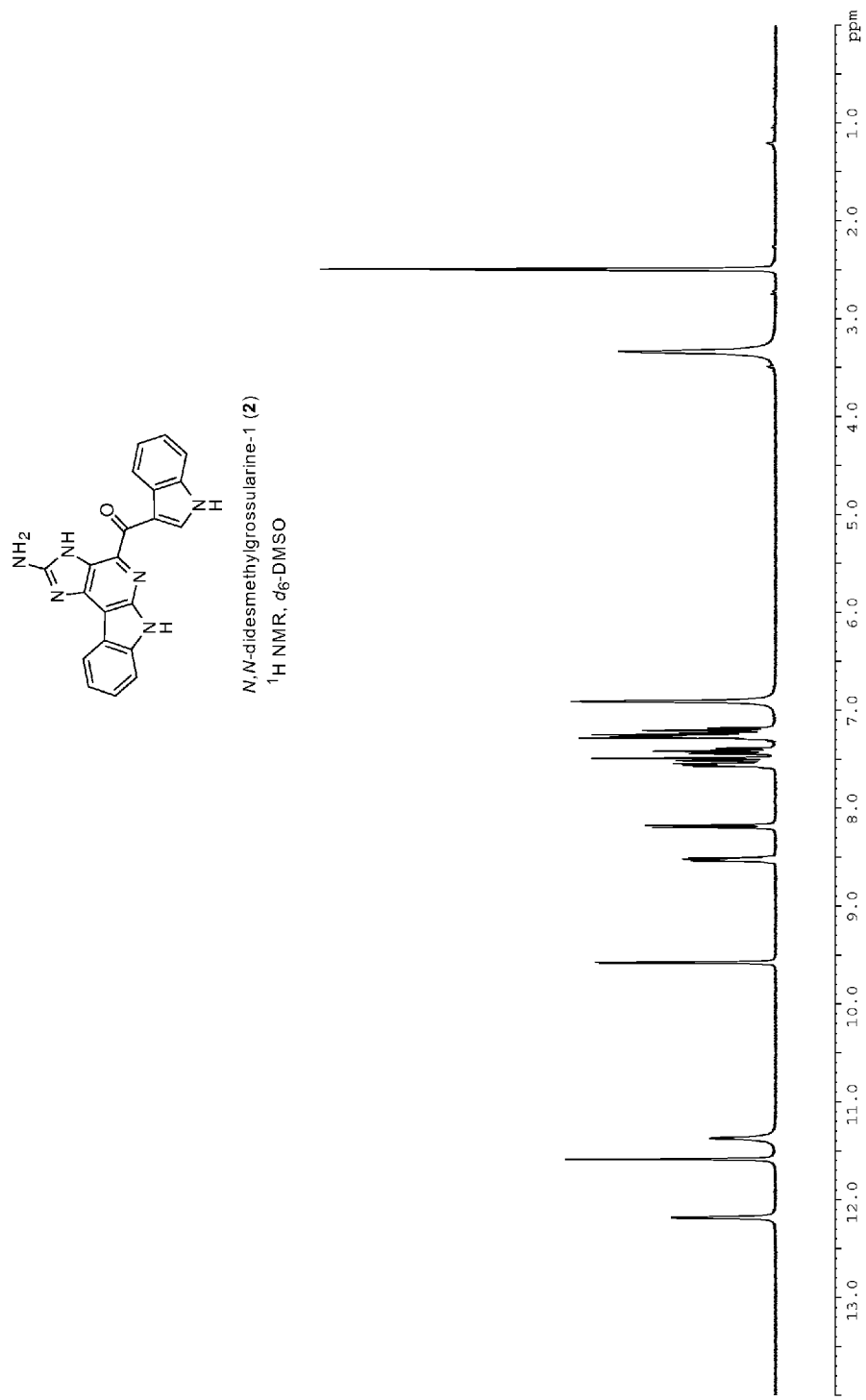
FIGS. 15 and 16 show spectral data for N,N-didesmethylgrossularine-1 2.
Figure 16:
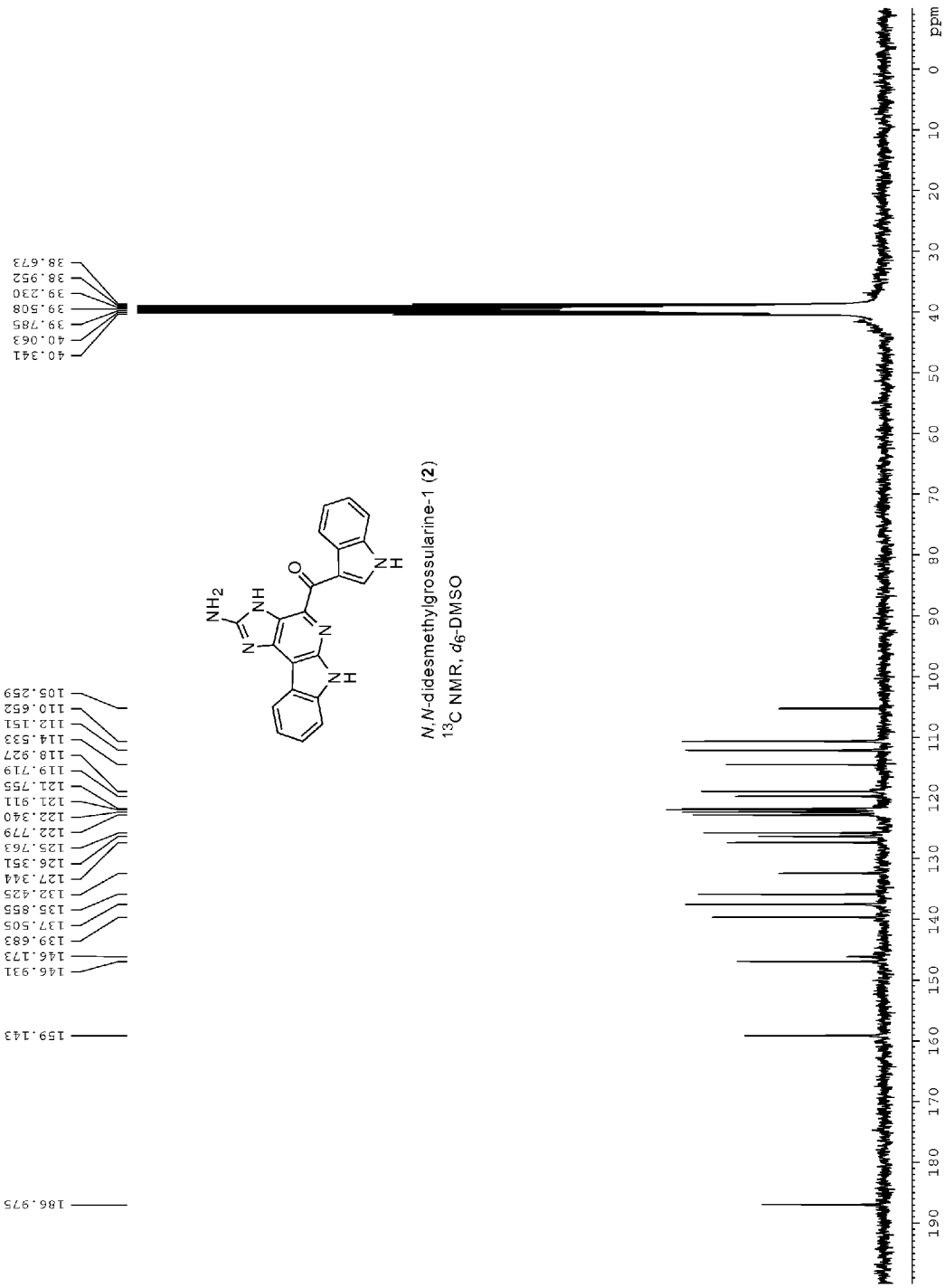

This example describes the synthesis of N,N-didesmethyl-grossularine-1 2 of FIG. 6. A solution of compound 10 (20 mg, 0.055 mmol) in 40 mL of EtOH-6N HCl (1:1) was stirred at 80° C. for 12 hours in sealed tube. Filtration of the reaction mixture afforded N,N-didesmethylgrossularine-1 2.HCl as a yellow solid in quantitative yield. The free base of N,N-didesmethylgrossularine-1 2 was obtained via neutralization with MeOH (sat. $NH_3$) followed by Flash silica gel chromatography ($CH_2Cl_2$/acetone 9:1). All spectral data of synthetic N,N-didesmethylgrossularine-1 2 were consistent with data reported for the natural product. Referring to FIGS. 15 and 16, Compound 2.HCl: $^{13}$H NMR (300 MHz, DMSO-$d_6$) δ 14.51 (br, 1H), 12.61 (s, 1H), 12.51 (bs, 1H), 12.36 (s, 1H), 9.49 (d, J=3.0 Hz, 1H), 8.73 (d, J=8.0 Hz, 1H), 8.51-8.48 (m, 1H), 8.33 (bs, 2H), 7.64-7.55 m, 3H), 7.36-7.27 (m, 3H); Compound 2: $^1$H NMR (300 MHz, DMSO-$d_6$) δ 12.18 (d, J=2.4 Hz, 1H), 11.59 (s, 1H), 11.37 (bs, 1H), 9.58 (d, J=2.9 Hz, 1H), 8.54-8.51 (m, 1H), 8.19 (d, J=7.6 Hz, 1H), 7.57-7.54 (m, 1H), 7.50 (d, J=8.0 Hz, 1H), 7.42 (t, J=7.7 Hz, 1H), 7.29-7.23 (m, 2H), 7.21 (t, J=7.6 Hz, 1H), 6.91 (bs, 2H): $^{13}$C NMR (100 MHz, DMSO-$d_6$) δ 187.0 (s), 159.1 (s), 146.9 (s), 146.2 (s), 139.7 (s), 137.5 (d), 135.9 (s), 132.4 (s), 127.3 (s), 126.3 (s), 125.8 (d), 122.8 (d), 122.3 (d), 121.9 (d), 121.8 (d), 119.7 (s), 118.9 (d), 114.5 (s), 112.2 (d), 110.7 (d), 105.3 (s); HRFABMS calcd for $C_{21}H_{15}N_6O$ 367.1307, found 367.1314.

Example 7

To determine if natural product grossularines-1 derivatives have anti-tumor activities in human cancer cells, DU145 human prostate cancer cells were treated with 30 μM compounds grossularine-1 1, N,N-didesmethylgrossularine-1 2, dimer 7, α-carboline 8, dimer 9, and imine 10 for 48 h, and MTS viability assays were performed. An MTS assay is a colorimetric experimental method to determine the number of viable cells in cytotoxicity assays and utilizes 3-(4,5-dimethylthiazol-2-yl)-5-(3-carboxymethoxyphenyl)-2-(4-sulfophenyl)-2H-tetrazolium, inner salt (MTS).

The experimental setup was as follows: DU145 human prostate cancer cells were obtained from ATCC and cultured in RPMI-1640 medium containing 10% fetal bovine serum (FBS), 100 units/ml of penicillin, and 100 μg/ml streptomycin. All cells were maintained in a 5% $CO_2$ atmosphere at 37° C. To determine the viability of the cells, MTS assays were performed as described by the supplier (Promega; Madison, Wis.). Briefly, cells (5,000/well) were seeded in 96-well plates and incubated overnight at 37° C. in 5% $CO_2$. Cells were treated for 48 h with 30 μM of each compound for initial screenings.

Figure 8:
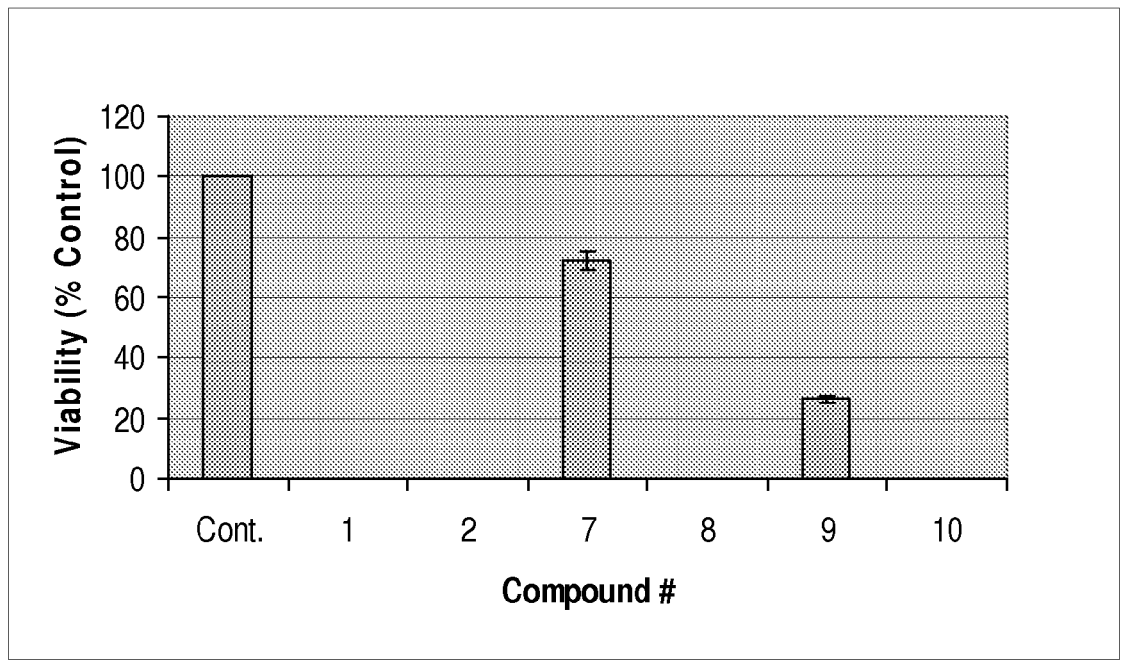
FIG. 8 shows that grossularine-1 derivatives have anti-tumor activities in human cancer cells.
Figure 9:
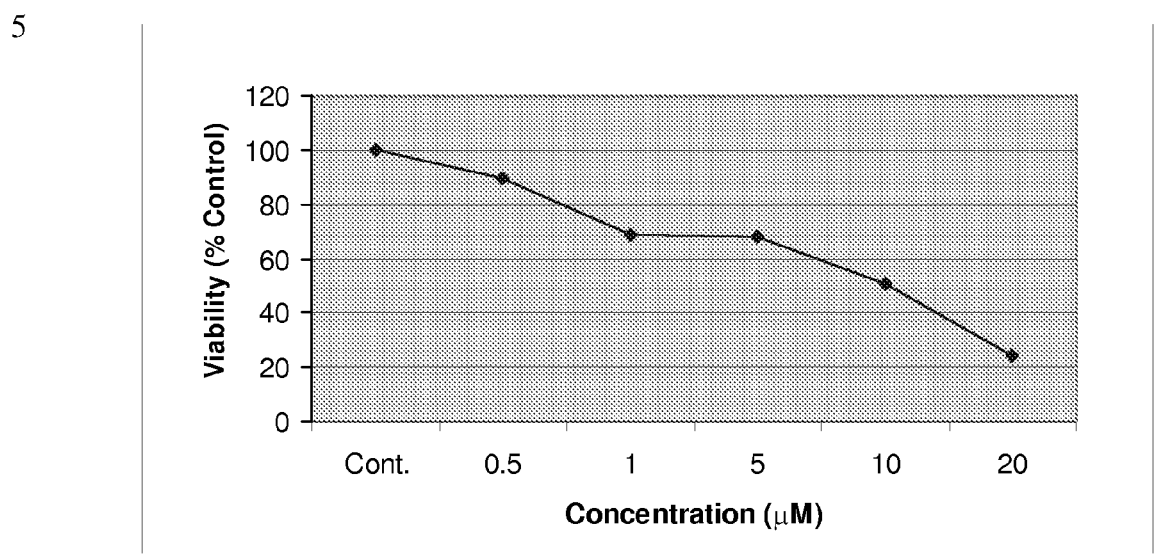
FIG. 9 shows the effects on cell viability in a dose-dependent manner and $IC_{50}$ value for grossularine-1 1.
Figure 10:
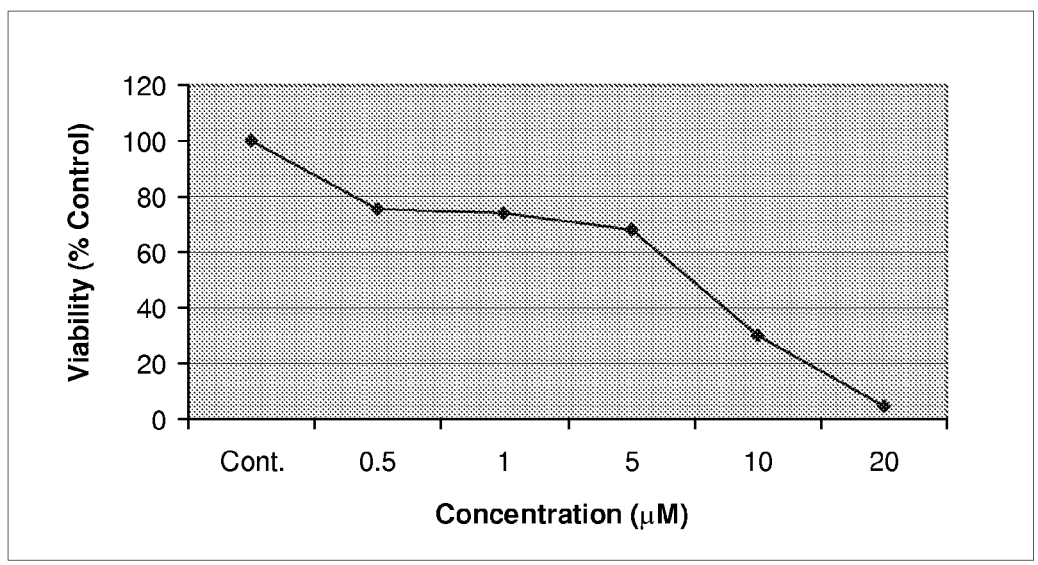
FIG. 10 shows the effects on cell viability in a dose-dependent manner and $IC_{50}$ value for N,N-didesmethylgrossularine-1 2.
Figure 11:
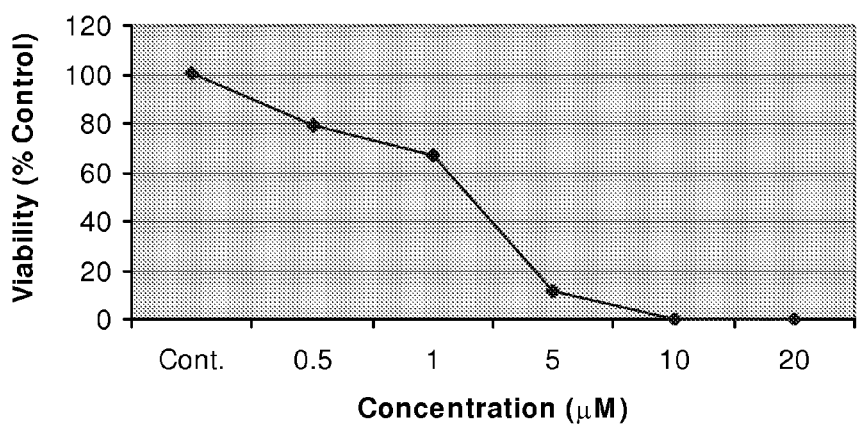
FIG. 11 shows the effects on cell viability in a dose-dependent manner and $IC_{50}$ value for α-carboline 8.
Figure 12:
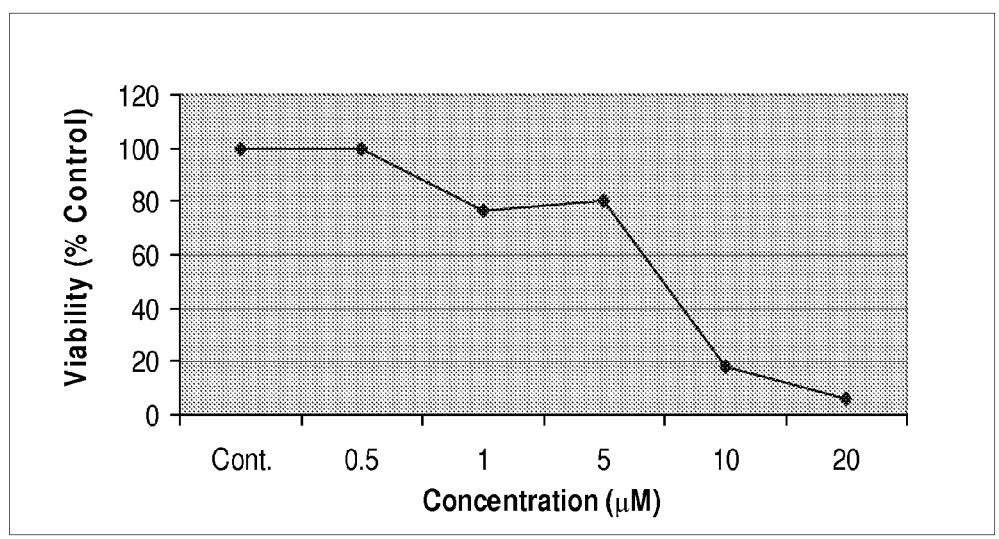
FIG. 12 shows the effects on cell viability in a dose-dependent manner and $IC_{50}$ value for imine 10.

Referring to FIG. 8, an MTS assay was performed to determine cell viability using 96-well plates. DU145 human cancer cells were treated with 30 μM grossularine-1 derivatives for initial screenings for 48 h. MTS dye was added to each well for 1 h. Cell viability was determined by tetrazolium conversion to its formazan dye and absorbance of formazan was measured at 490 nm. Values are the mean ±SD. Each experiment was performed in quadruplicate.

As shown in FIG. 8, treatment with compounds grossularine-11, N,N-didesmethylgrossularine-1 2, α-carboline 8, and imine 10 resulted in complete loss of cell viability. However, dimer 7 and dimer 9, intermediates formed during synthesis of grossularines-1, showed less cytotoxicity than grossularines-1 derivatives. Compounds grossularine-1 1 and N,N-didesmethylgrossularine-1 2 have similar structures yet differ in the degree of methylation. α-carbolines 8 and 10 are imino analogs of 1 and 2, respectively.

To determine $IC_{50}$ values for compound grossularine-11, N,N-didesmethylgrossularine-1 2, α-carbolines 8 and 10, cells were treated in dose-dependent manner at 0.1 to 20 μM concentration for 48 h. Dimethyl sulfoxide (DMSO) was used as the vehicle control. MTS dye was added to each 96-well plate well for one hour. Cell viability was determined by tetrazolium conversion to its formazan dye and absorbance of formazan was measured at 490 nm using an automated ELISA plate reader. The production of formazan dye was directly proportional to the number of living cells.

Referring to FIGS. 9-12, all compounds 1, 2, 8, and 10 had effects on cell viability in a dose-dependent manner, showing that their $IC_{50}$ values are 10.3 μM, 7.3 μM, 1.8 μM, and 7.6 μM, respectively. In comparison of structures α-carboline imines 8 and 10, possessing methyl moieties at R positions were more favorable than hydrogen in cytotoxicity assays.

Example 8

Figure 31:
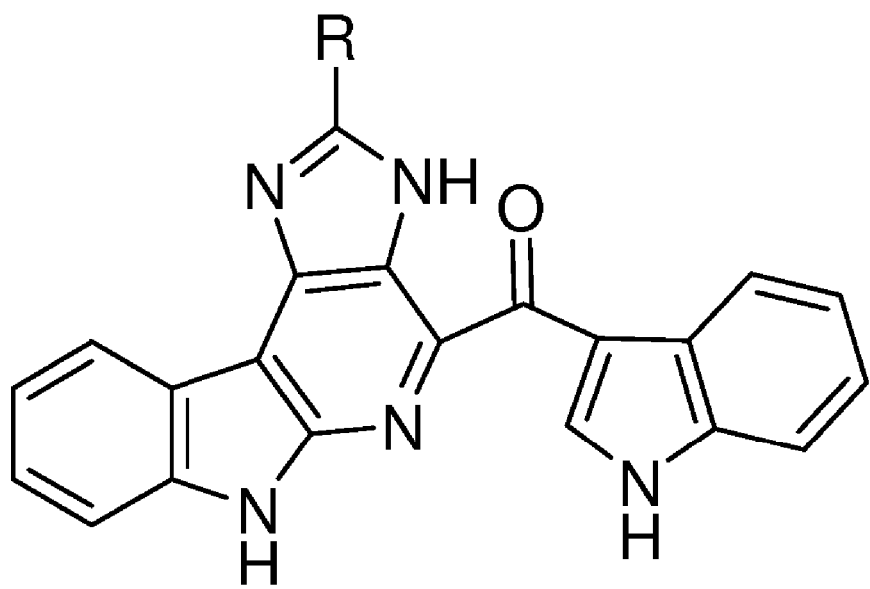
FIG. 31 shows N,N-diethyl-pre-grossularine-1 11 and piperidinyl-pre-grossularine-1 13.
Figure 32:
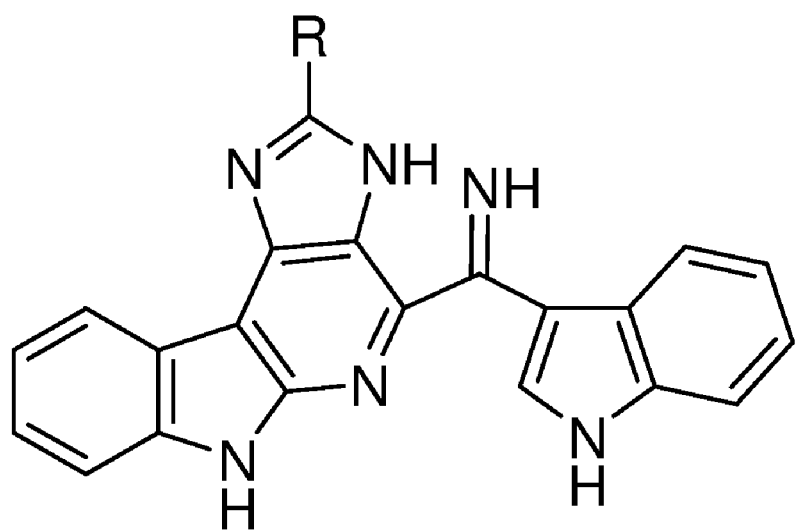
FIG. 32 shows N,N-diethyl-grossularine-1 12 and piperidinyl-grossularine-1 14.
Figure 32:
Figure 33:
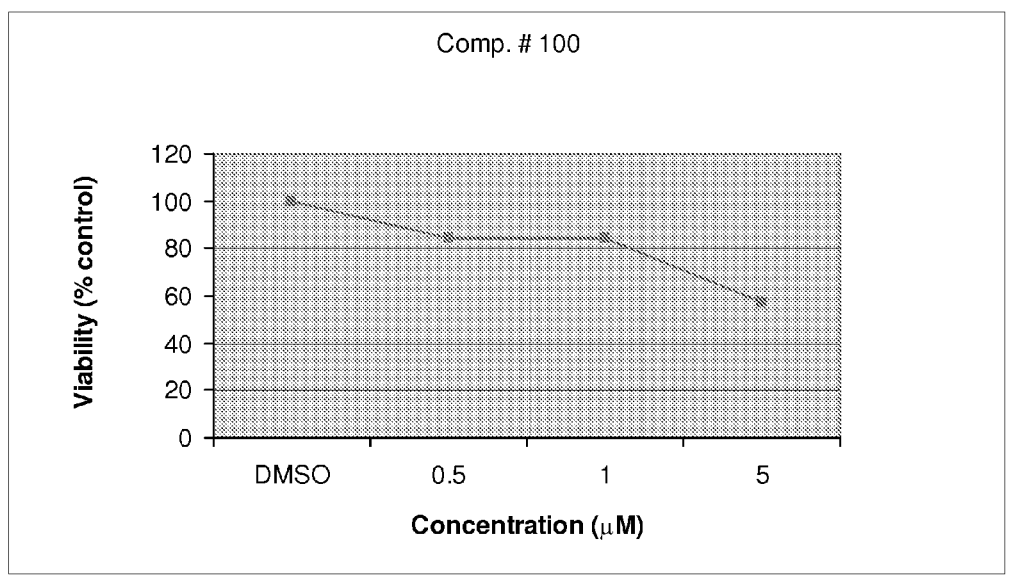
FIG. 33 shows the effects on cell viability in a dose-dependent manner for N,N-diethyl-pre-grossularine-1 11.
Figure 34:
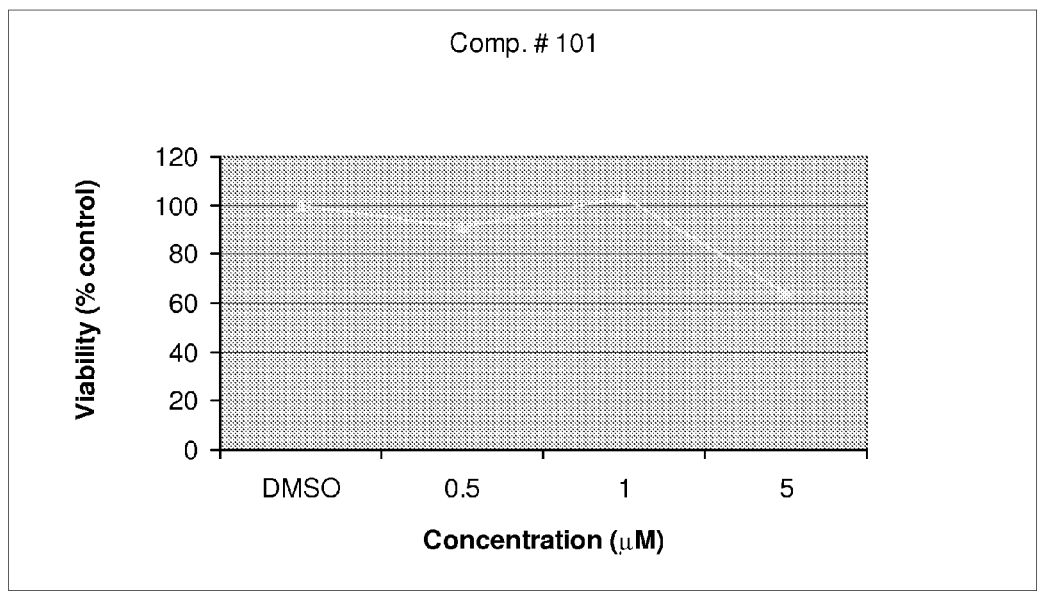
FIG. 34 shows the effects on cell viability in a dose-dependent manner for N,N-diethyl-grossularine-1 12.
Figure 35:
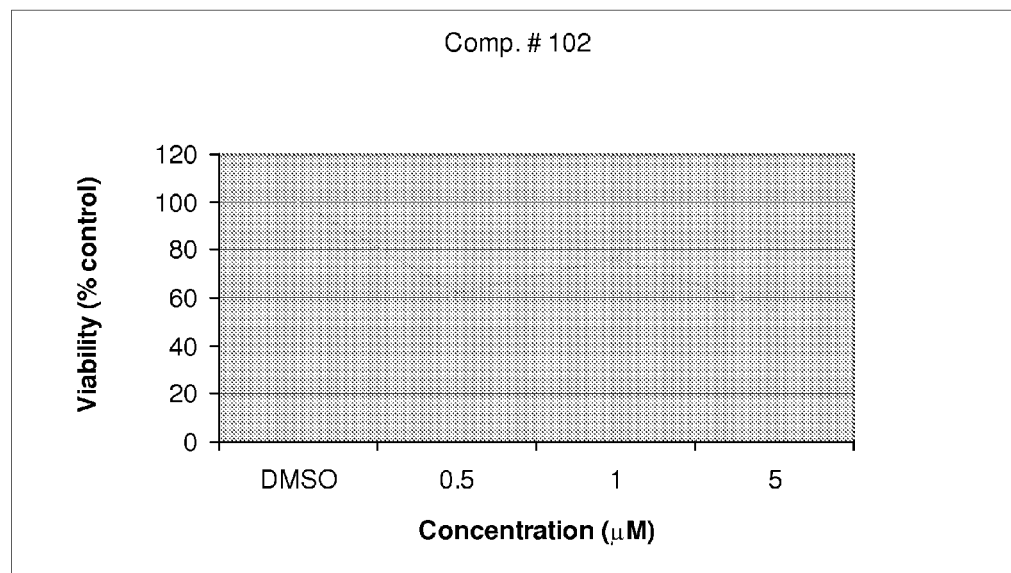
FIG. 35 shows the effects on cell viability in a dose-dependent manner for piperidinyl-pre-grossularine-1 13.
Figure 36:
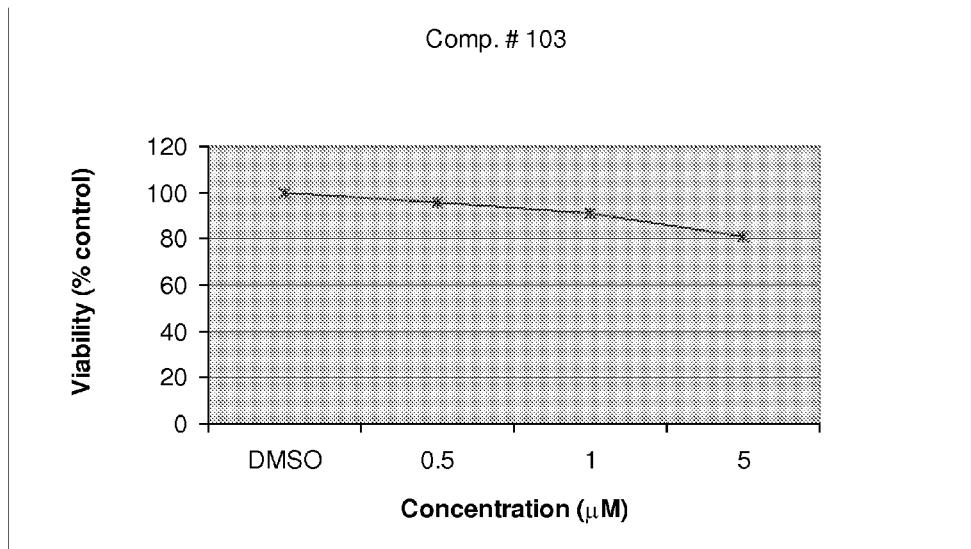
FIG. 36 shows the effects on cell viability in a dose-dependent manner for piperidinyl-grossularine-1 14.
Figure 37:
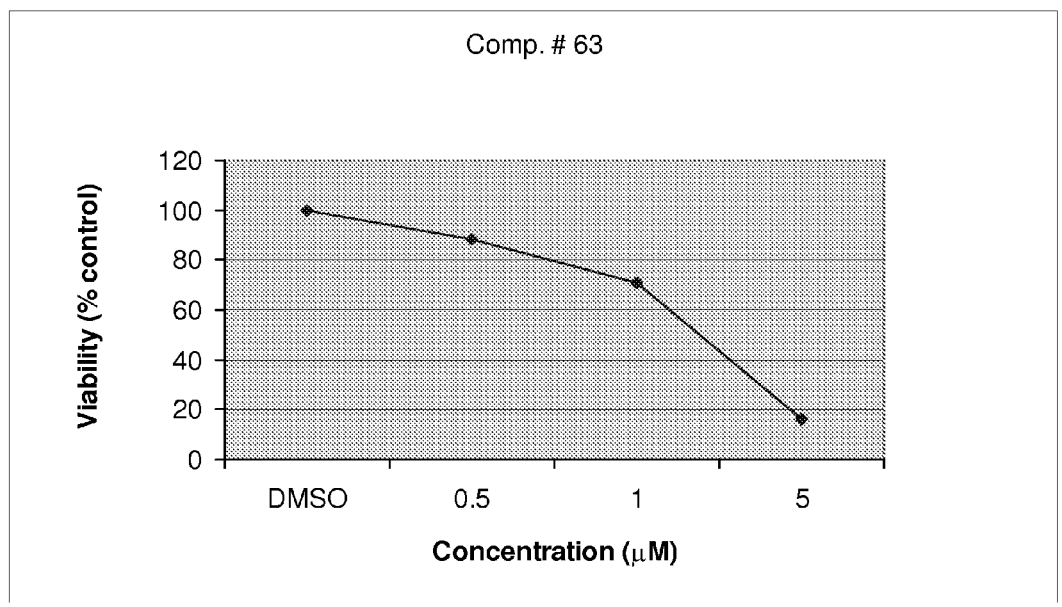
FIG. 37 again shows the effects on cell viability in a dose-dependent manner for grossularine-1 1 (for comparison with FIGS. 33-36).

Referring to FIG. 31, in experiments similar to those of Example 7, analogs N,N-diethyl-pre-grossularine-1 11, N,N-diethyl-grossularine-1 12, piperidinyl-pre-grossularine-1 13, and piperidinyl-grossularine-1 14 were tested and compared to grossularine-1 1 to determine if the analogs have anti-tumor activities in human cancer cells. DU145 cells (5,000 cells/each well) were treated in dose-dependent manner for 48 h. Then, MTS assay was performed with four samples for each experiment.

It is thus shown that imino grossularines-1 derivatives, which are novel alpha-carboline imino based heterocycles, have cytotoxic effects in human cancer cells. These results demonstrate their potential as novel anti-tumor therapeutic agents.

REFERENCES

[1] C. Moquin-Pattey, M. Guyot *Tetrahedron* 1989, 45, 3445-3450; A. Loukaci, M. Guyot *Mag. Res. Chem.* 1996, 34, 143-145; N. Helbecque, C. Moquin, J.-L. Bernier, E. Morel, M Guyot, J.-P. Henichart *Cancer Biochem. Biophys.* 1987, 9, 271-279.

[2] S. A. Abas, M. B. Hossain, D. van der Helm, F. J. Schmitz, M. Laney, R. Cabuslay, R. C. Schatzman *J. Org. Chem.* 1996, 61, 2709-2712.

[3] T. Choshi, S. Yamada, E. Sugino, T. Kuwada, S. Hibino *J. Org. Chem.* 1995, 60, 5899-5904.

[4] P. Molina, P. M. Fresneda, M. A. Sanz, C. Foces-Foces, M. C. R. de Arellano *Tetrahedron* 1998, 54, 9623-9638.

[5] F. Y. Miyake, K. Yakushijin, D. A. Horne *Org. Lett.* 2000, 2, 2121-2123; F. Y. Miyake, K. Yakushijin, D. A. Horne *Org. Lett.* 2000, 2, 3185-3187; c) F. Y. Miyake, K. Yakushijin, D. A. Horne *Org. Lett.* 2002, 2, 941-943.

[6] M. Guyot, M. Meyer *Tetrahedron Lett.* 1986, 27, 2621-2622.

[7] A. Olofson, K. Yakushijin, D. A. Horne *J. Org. Chem.* 1998, 63, 1248-1253; A. C. Barrios-Sosa, K. Yakushijin, D. A. Horne *J. Org. Chem.* 2000, 65, 610-611; A. C. Barrios-Sosa, K. Yakushijin, D. A. Horne *J. Org. Chem.* 2002, 67, 4498-4500.

[8] A. Lawson *J. Chem. Soc.* 1956, 307-310; G. C. Lancini, E. Lazzari *J. Heterocycl. Chem.* 1966, 3, 152-166.

[9] A. Dalkafouki, J. Ardisson, N. Kunesch, L. Lacombe, J. E. Poisson *Tetrahedron Lett.* 1991, 32, 5325-5328.

[10] B. R. Lahue, Z.-K. Wan, J. K. Snyder *J. Org. Chem.* 2003, 68, 4345-4354.

[11] For an example of unsymmetrical dimer formation resulting from autooxidation of the indolic neurotoxin 5,6-dihydroxytryptamine, see S. Singh, J.-F. Jen, G. Dryhurst *J. Org. Chem.* 1990, 55, 1484-1489.

Papers and patents listed in the disclosure are expressly incorporated by reference in their entirety. It is to be understood that the description, specific examples, and figures, while indicating preferred embodiments, are given by way of illustration and exemplification and are not intended to limit the scope of the present invention. Various changes and modifications within the present invention will become apparent to the skilled artisan from the disclosure contained herein and may be made without departing from the spirit of the present invention. Therefore, the spirit and scope of the appended claims should not be limited to the description of the preferred versions contained herein.

The invention claimed is:

1. A method of synthesizing grossularine-1

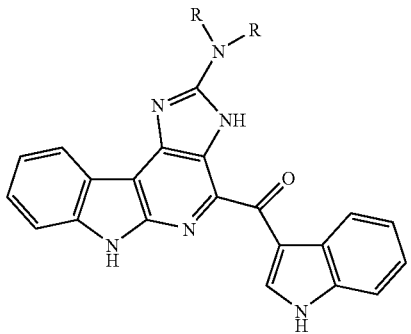

(R = Me)

comprising:

condensing oxotryptamine

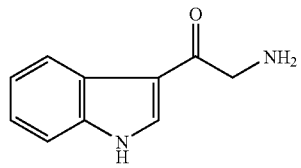

and dimethylcynanmide in the absence of air to produce 2-dimethylamino-4-(3-indolyl)imidazole

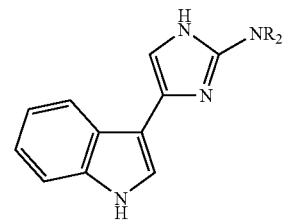

(R=Me) as an HCl salt;

exposing 2-dimethylamino-4-(3-indolyl)imidazole

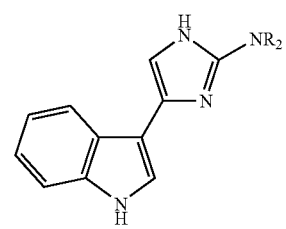

(R=Me) HCl salt to an ammonia saturated methanol solution in air to produce α-carboline imine and exposing α-carboline imine

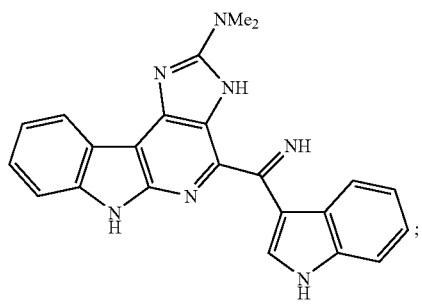

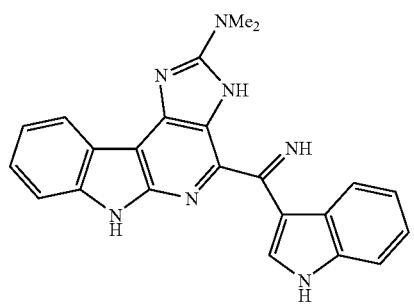

to hydrolysis conditions to produce grossularine-1

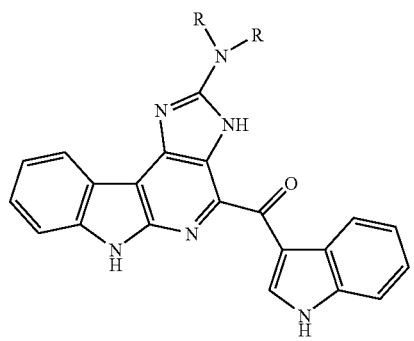

(R=Me).

2. A method of synthesizing N,N-didesmethylgrossularine-1

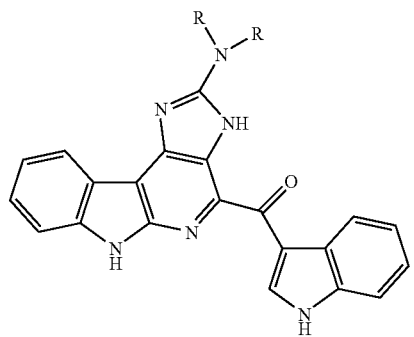

(R=H) comprising:
condensing oxotryptamine

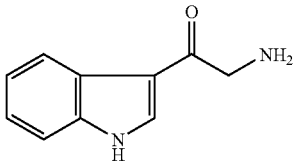

and cynanmide in the absence of air to produce 2-amino-4-(3-indolyl)imidazole

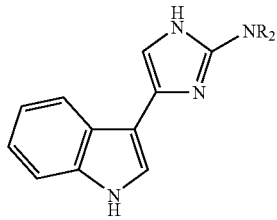

(R=H);
exposing 2-amino-4-(3-indolyl)imidazole

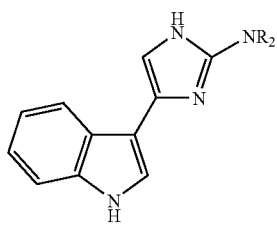

(R=H) to an ammonia saturated methanol solution in air to produce imine

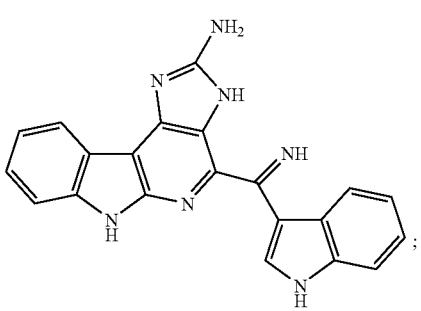

and
exposing imine

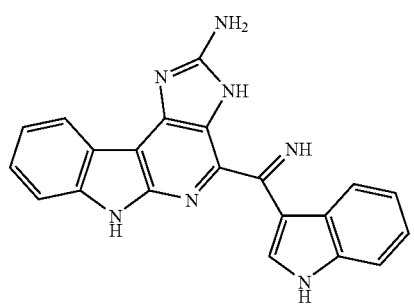
to hydrolysis conditions to produce N,N-didesmethyl-grossularine-1
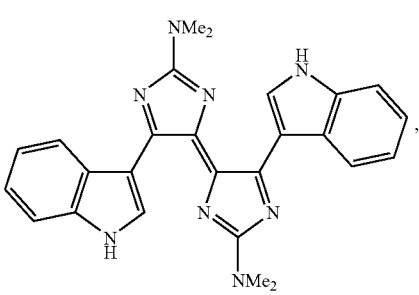
(R=H) dimer
dimer
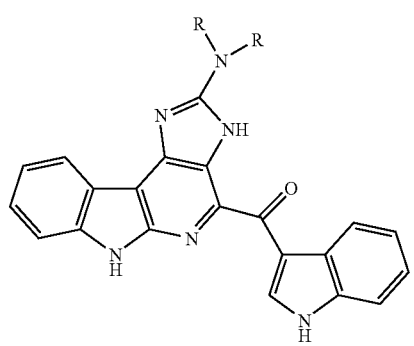
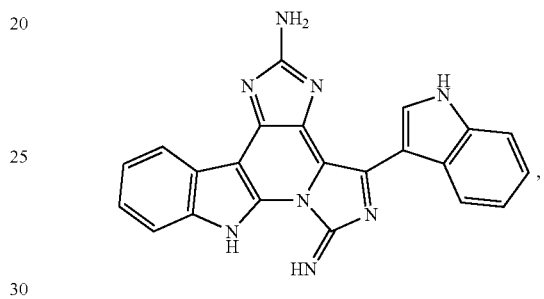
α-carboline mine
(R=H).
3. A compound selected from the group consisting of 2-dimethylamino-4-(3-indolyl)imidazole
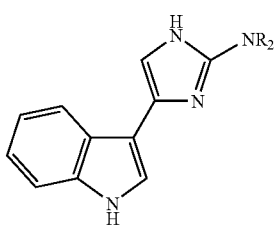
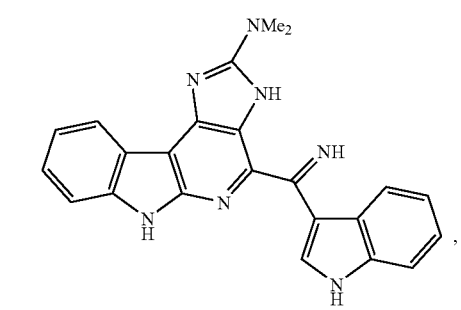
(R=Me), 2-amino-4-(3-indolyl)imidazole
and imine
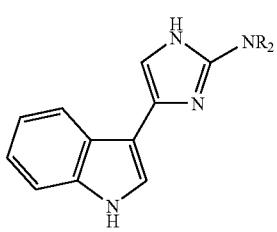
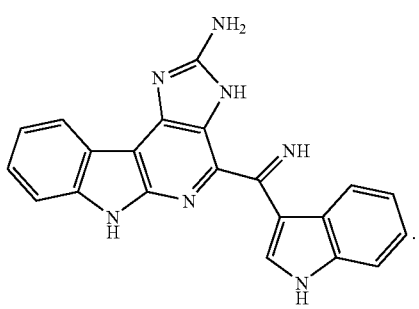

4. A method of synthesis comprising:

(1) reacting a first compound

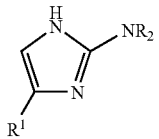

with a second compound

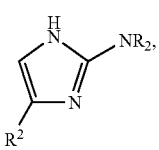

wherein $R^1 = $ 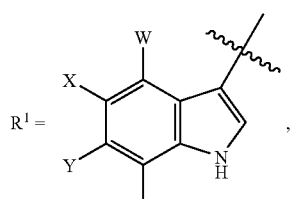, $R^2 = $ 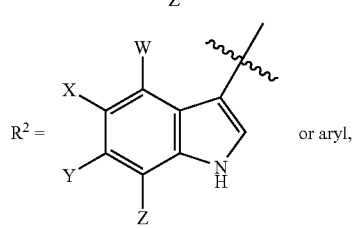 or aryl, and

R is hydrogen, and wherein W, X, Y, and Z are each selected from the group consisting of hydrogen, alkyl, halogen, aryl, OR', or SR' wherein R' is hydrogen, alkyl or aryl, to form a third compound having the formula:

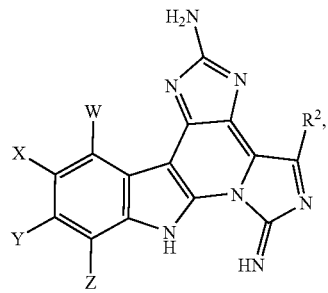

and/or a fourth compound having the formula:

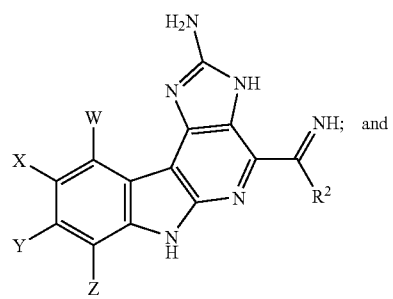

(2) hydrolyzing the fourth compound to form:

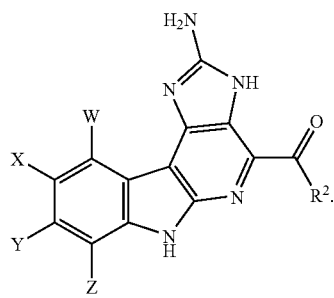

5. The method of claim 4 wherein reaction step (1) is performed in the presence of a methanol and ammonia solution.

6. The method of claim 4 wherein reaction step (1) is performed in the presence of a methanol solution substantially saturated with ammonia.

7. A method of synthesis comprising:

(1) reacting a first compound

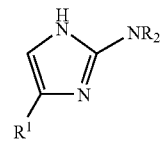

with a second compound

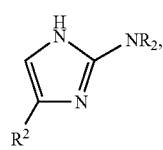

wherein

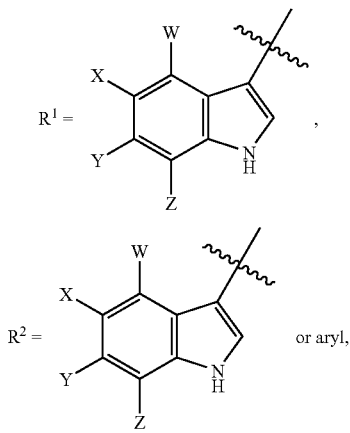

and

R is alkyl or aryl, and wherein W, X, Y, and Z are each selected from the group consisting of hydrogen, alkyl, halogen, aryl, OR', or SR', wherein R' is hydrogen, alkyl or aryl, to form a third compound having the formula:

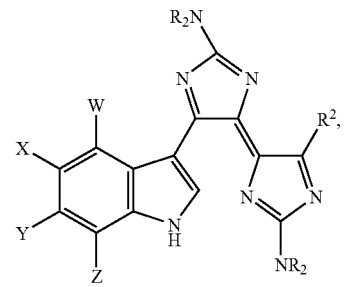

and/or a fourth compound having the formula:

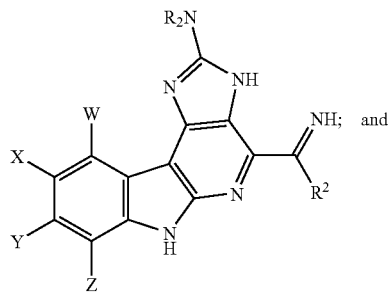

(2) hydrolyzing the fourth compound to form:

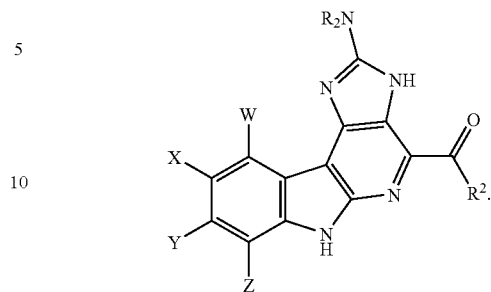

8. The method of claim 7 wherein reaction step (1) is performed in the presence of a methanol and ammonia solution.

9. The method of claim 7 wherein reaction step (1) is performed in the presence of a methanol solution substantially saturated with ammonia.

10. A method of synthesis comprising:
(1) reacting a first compound

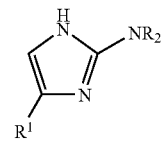

with a second compound

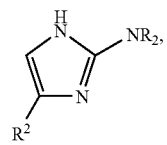

wherein

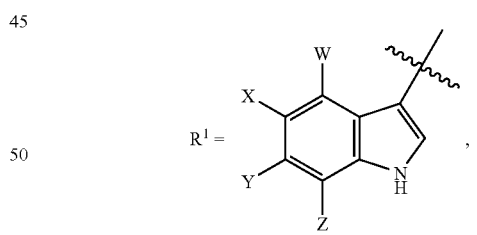

and
R is hydrogen, and wherein W, X, Y, and Z are each selected from the group consisting of hydrogen, alkyl, halogen, aryl, OR', or SR', wherein R' is hydrogen, alkyl or aryl, to form a third compound having the formula:

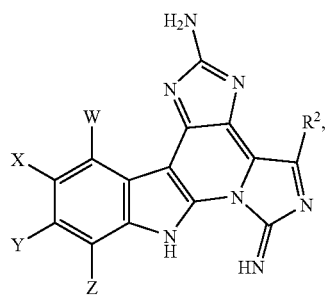

and/or a fourth compound having the formula:

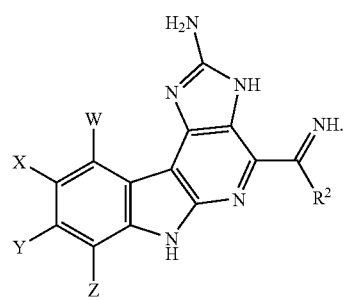

11. The method of claim 10 wherein reaction step (1) is performed in the presence of a methanol and ammonia solution.

12. The method of claim 10 wherein reaction step (1) is performed in the presence of a methanol solution substantially saturated with ammonia.

13. A method of synthesis comprising:
(1) reacting a first compound

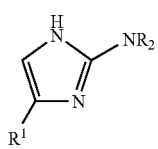

with a second compound

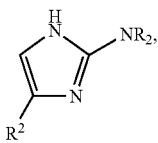

wherein $R^1 =$ 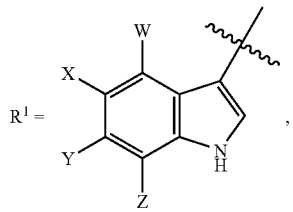, $R^2 =$ 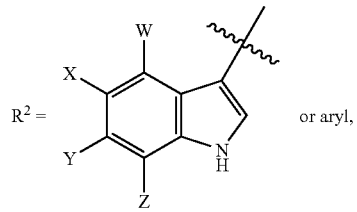 or aryl, and

R is alkyl or aryl, and wherein W, X, Y, and Z are each selected from the group consisting of hydrogen, alkyl, halogen, aryl, OR', or SR', wherein R' is hydrogen, alkyl or aryl, to form a third compound having the formula:

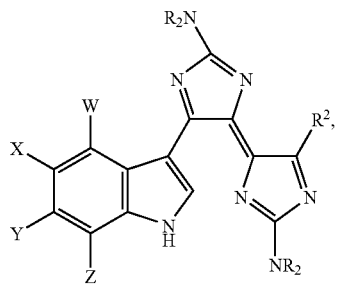

and/or a fourth compound having the formula:

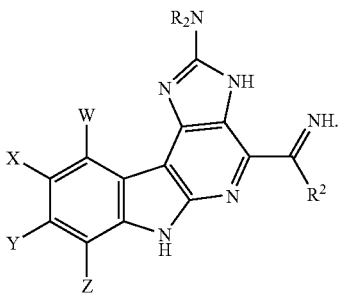

14. The method of claim 13 wherein reaction step (1) is performed in the presence of a methanol and ammonia solution.

15. The method of claim 13 wherein reaction step (1) is performed in the presence of a methanol solution substantially saturated with ammonia.

16. A compound selected from the group consisting of N,N-diethyl-pre-grossulariine-1

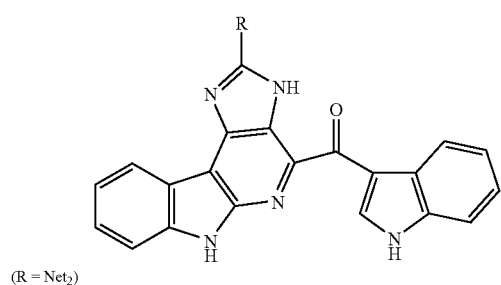
(R = NEt₂)
N,N-diethyl-grossularine-1
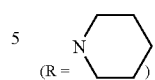
piperidinyl-grossularine-1
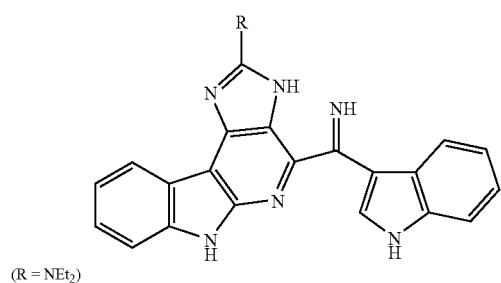
(R = NEt₂)
piperidinyl-pre-grossularine-1
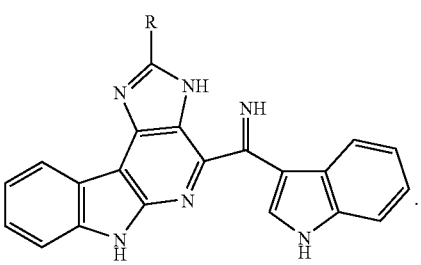
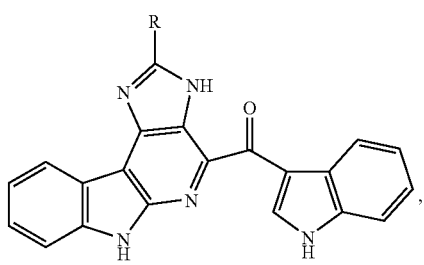
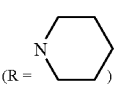
* * * * *